US008673846B2

(12) United States Patent
Yoshida et al.

(10) Patent No.: US 8,673,846 B2
(45) Date of Patent: Mar. 18, 2014

(54) CELL PROLIFERATION-PROMOTING PEPTIDE AND USE THEREOF

(75) Inventors: Tetsuhiko Yoshida, Tsukuba (JP); Nahoko Kobayashi, Tsukuba (JP); Mikio Niwa, Tsukuba (JP); Chikara Shinohara, Gamagori (JP); Masatoki Watanabe, Gamagori (JP); Ken-ichiro Hata, Gamagori (JP)

(73) Assignees: Toagosei Co. Ltd., Tokyo (JP); Japan Tissue Engineering Co., Ltd., Aichi (JP)

( * ) Notice: Subject to any disclaimer, the term of this patent is extended or adjusted under 35 U.S.C. 154(b) by 0 days.

(21) Appl. No.: 13/503,220

(22) PCT Filed: Oct. 28, 2010

(86) PCT No.: PCT/JP2010/069165
§ 371 (c)(1),
(2), (4) Date: Apr. 20, 2012

(87) PCT Pub. No.: WO2011/052679
PCT Pub. Date: May 5, 2011

(65) Prior Publication Data
US 2012/0208752 A1 Aug. 16, 2012

(30) Foreign Application Priority Data
Nov. 2, 2009 (JP) ................................. 2009-252010

(51) Int. Cl.
*A61K 38/02* (2006.01)
*A61K 38/18* (2006.01)
*C12N 5/02* (2006.01)

(52) U.S. Cl.
USPC ........................... 514/1.2; 514/21.2; 530/300

(58) Field of Classification Search
None
See application file for complete search history.

(56) References Cited

U.S. PATENT DOCUMENTS

| | | | |
|---|---|---|---|
| 4,867,975 A | 9/1989 | Gelb, Jr. | |
| 6,037,521 A | 3/2000 | Sato et al. | |
| 6,340,583 B1 | 1/2002 | Yan et al. | |
| 6,403,353 B1 | 6/2002 | Yan et al. | |
| 6,423,684 B1 * | 7/2002 | Mochly-Rosen et al. | 435/7.1 |
| 2003/0125242 A1 | 7/2003 | Rosenecker et al. | |
| 2003/0166215 A1 | 9/2003 | Yan et al. | |
| 2003/0229202 A1 | 12/2003 | Guo et al. | |
| 2004/0175751 A1 | 9/2004 | Yan et al. | |
| 2004/0186052 A1 | 9/2004 | Iyer et al. | |
| 2004/0226056 A1 | 11/2004 | Roch et al. | |
| 2006/0100134 A1 | 5/2006 | Guo et al. | |
| 2006/0166917 A1 | 7/2006 | Lindeman et al. | |
| 2006/0270834 A1 | 11/2006 | Kanno | |
| 2007/0065941 A1 | 3/2007 | Kondo et al. | |
| 2008/0076145 A1 | 3/2008 | Cummings et al. | |
| 2009/0253618 A1 | 10/2009 | Kanno et al. | |
| 2010/0297758 A1 | 11/2010 | Yoshida et al. | |
| 2012/0035112 A1 | 2/2012 | Yoshida et al. | |
| 2012/0122210 A1 | 5/2012 | Yoshida et al. | |
| 2012/0122225 A1 | 5/2012 | Kobayashi et al. | |
| 2013/0005034 A1 | 1/2013 | Yoshida et al. | |
| 2013/0079273 A1 | 3/2013 | Yoshida et al. | |

FOREIGN PATENT DOCUMENTS

| | | | |
|---|---|---|---|
| EP | 1 918 297 A1 | 5/2008 | |
| JP | A-7-132033 | 5/1995 | |
| JP | A-9-323928 | 12/1997 | |
| JP | A-2001-199997 | 7/2001 | |
| JP | A-2003-137899 | 5/2003 | |
| JP | A-2004-357543 | 12/2004 | |
| JP | A-2005-154338 | 6/2005 | |
| JP | A-2005-330206 | 12/2005 | |
| JP | B2-3854995 | 12/2006 | |
| JP | A-2007-145761 | 6/2007 | |
| JP | A-2007-159429 | 6/2007 | |
| JP | A-2009-209064 | 9/2009 | |
| JP | A-2011-016763 | 1/2011 | |
| WO | WO 02/18572 A2 | 3/2002 | |
| WO | WO 02/077171 A2 | 10/2002 | |
| WO | WO 03/076561 A2 | 9/2003 | |
| WO | WO 2004/056854 A1 | 7/2004 | |
| WO | WO 2005/086800 A2 | 9/2005 | |
| WO | WO 2007/010989 A1 | 1/2007 | |
| WO | WO 2007/149293 A2 | 12/2007 | |
| WO | WO 2008/008569 A2 | 1/2008 | |
| WO | WO 2009/093692 A1 | 7/2009 | |
| WO | WO 2010/117079 A1 | 10/2010 | |
| WO | WO 2010117078 A1 * | 10/2010 | ............... C07K 7/08 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Goyal et al, Phosphorylation-dependent Regulation of Unique Nuclear and Nucleolar Localization Signals of LIM Kinase 2 in Endothelial Cells, Journal of Biological Chemistry, 2006, 281, pp. 25223-25230.*
Machine translated WO 2010117078 A1, enclosed, pp. 1-18.*
Emmott et al., "Nucleolar Targeting: The Hub of the Matter," *EMBO Reports*, 2009, pp. 231-238, vol. 10, No. 3, European Molecular Biology Organization.

(Continued)

*Primary Examiner* — Julie Ha
*Assistant Examiner* — Li Ni Komatsu
(74) *Attorney, Agent, or Firm* — Oliff PLC

(57) ABSTRACT

A cell proliferation promoter includes, as an active ingredient, an artificially synthesized peptide that includes (A) an amino acid sequence constituting a membrane-permeable peptide and (B) an amino acid sequence selected from SEQ ID NOs: 19 to 103 or an amino acid sequence formed by substituting, deleting and/or adding one or several amino acid residues in the selected amino acid sequence.

12 Claims, 3 Drawing Sheets

(56) References Cited

OTHER PUBLICATIONS

Hilton et al., "Twenty Proteins Containing a C-Terminal SOCS Box From Five Structural Classes," *Proc. Natl. Acad. Sci.*, Jan. 1998, pp. 114-119, vol. 95, The National Academy of Sciences.

Kamura et al., "The Elongin BC Complex Interacts with the Conserved SOCS-Box Motif Present in Members of the SOCS, ras, WD-40 repeat, and Ankyrin Repeat Families," *Genes & Development*, 1998, pp. 3872-3881, vol. 12, Cold Spring Harbor Laboratory Press.

Yu et al., "Selective Assembly of HIV-1 Vif-Cul5-ElonginB-ElonginC E3 Ubiquitin Ligase Complex Through a Novel SOCS Box and Upstream Cysteines," *Genes & Development*, 2004, pp. 2867-2872, vol. 18, Cold Spring Harbor Laboratory Press.

Kamura et al., "VHL-Box and SOCS-Box Domains Determine Binding Specificity for Cul2-Rbxl and Cul5-Rbx2 Modules of Ubiquitin Ligases," *Genes & Development*, 2004, pp. 3055-3065, vol. 18, Cold Spring Harbor Laboratory Press.

Liu et al., "Rack 1 Competes with HSP90 for Binding to HIF-1α and is Required for $O_2$-Independent and HSP90 Inhibitor-Induced Degradation of HIF-1α," *Molecular Cell*, Jan. 26, 2007, pp. 207-217, vol. 25, Elsevier Inc.

Liu et al., "Calcineurin Promotes Hypoxia-Inducible Factor 1 α Expression by Dephosphorylating RACK1 and Blocking Rack1 Dimerization," *Journal of Biological Chemistry*, Dec. 21, 2007, pp. 37064-37073, vol. 282, No. 51, The American Society for Biochemistry and Molecular Biology, Inc.

Liu et al., "Rack1 vs. HSP90: Competition for HIF-1α Degradation vs. Stablization," *Cell Cycle*, 2007, pp. 656-659, vol. 6, No. 6, Landes Bioscience.

Kile et al., "The Suppressors of Cytokine Signalling (SOCS)," *Cellular and Molecular Life Sciences*, 2001, pp. 1627-1635, vol. 58, Birkhäuser Verlag, Basel.

Jan. 18, 2011 International Search Report issued in International Patent Application No. PCT/JP2010/069165.

Jun. 12, 2012 International Preliminary Report on Patentability issued in International Patent Application No. PCT/JP2010/069165.

Bochkov et al., "Phylogenetic Analysis of Partial S1 and N Gene Sequences of Infections Bronchitis Virus Isolates from Italy Revealed Genetic Diversity and Recombination," Virus Genes, vol. 35, pp. 65-71, 2007.

Boursnell et al., "Sequences of the Nucleocapsid Genes from Two Strains of Avian Infectious Bronchitis Virus," J. Gen. Virol., vol. 66, pp. 573-580, 1985.

Cserpán et al., "The Mechanism of Nuclear Transport of Natural or Artificial Transport Substrates in Digitonin-Permeabilized Cells," Journal of Cell Science, vol. 108, pp. 1849-1861, 1995.

Eiges et al., "Establishment of Human Embryonic Stem Cell-Transfected Clones Carrying a Marker for Undifferentiated Cells," Current Biology, vol. 11, pp. 514-518, 2001.

Fang et al., "Selection of and Recombination between Minor Variants Lead to the Adaptation of an Avian Coronavirus to Primate Cells," Biochemical and Biophysical Research Communications, vol. 336, pp. 417-423, 2005.

Futaki et al., "Intracellular Protein Delivery Using Membrane-Permeable Peptides," Seibutsu to Kagaku, vol. 43, No. 10, pp. 649-653, 2005, with English-language translation.
Kang et al., "The Precursor of Alzheimer's Disease Amyloid A4 Protein Resembles a Cell-Surface Receptor," Nature, vol. 325, pp. 733-736, Feb. 19, 1987.
Kobayashi et al., "Nucleolar Localization Signals of LIM Kinase 2 Function as a Cell-Penetrating Peptide," Protein & Peptide Letters, vol. 17, pp. 1480-1488, 2010.
Kwak et al., "Amyloid Precursor Protein Regulates Differentiation of Human Neural Stem Cells," Stem Cells Dev., vol. 15, No. 3, pp. 381-389, 2006.
Martoglio et al., "Signal Sequences: More than just Greasy Peptides," Trends in Cell Biology, vol. 8, pp. 410-415, Oct. 1998.
Marutle et al., "Modulation of Human Neural Stem Cell Differentiation in Alzheimer (APP23) Transgenic Mice by Phenserine," Proc. Natl. Acad. USA, vol. 104, No. 30, pp. 12506-12511, Jul. 24, 2007.
NCBI database Accession No. Q1M2X0, p. 1, accessed Nov. 7, 2012.
Pokorska et al., "The Analysis of the Transcriptional Activator PrnA Reveals a Tripartite Nuclear Localisation Sequence," J. Mil. Biol., vol. 298, pp. 585-596, 2000.
Reed et al., "Delineation and Modelling of a Nucleolar Retention Signal in the Coronavirus Nucleocapsid Protein," Traffic, vol. 7, pp. 833-848, 2006.
Sugaya et al., "Practical Issues in Stem Cell Therapy for Alzheimer's Disease," Curr. Alzheimer Res., vol. 4, No. 4, pp. 370-377, 2007 (Abstract Only).
Takei et al., "Possible Involvement of a Pertussis Toxin-Sensitive GTP-Binding Protein in Protein Transport into Nuclei Isolated from Rat Liver," J. Biochem., vol. 115, pp. 578-583, 1994.
Mar. 1, 2011 European Search Report issued in European Application No. 09 704 366.5.
Dec. 5, 2011 European Office Action issued in European Application No. 09 704 366.5.
Apr. 7, 2009 International Search Report issued in International Application No. PCT/2009/051082.
Jul. 13, 2010 International Search Report issued in International Application No. PCT/JP2010/056510 (with translation).
Oct. 5, 2010 International Search Report issued in International Patent Application No. PCT/JP2010/062691 (with translation).
Oct. 5, 2010 International Search Report issued in International Patent Application No. PCT/JP2010/062693 (with translation).
Jul. 19, 2011 International Search Report issued in International Application No. PCT/JP2011/062809.
Jan. 8, 2013 International Preliminary Report on Patentability and Written Opinion issued in International Application No. PCT/JP2011/062809.
Mar. 29, 2010 International Preliminary Report on Patentability and Written Opinion issued in International Application No. PCT/JP2009/051082.
Aug. 17, 2011 Office Action issued in U.S. Appl. No. 12/864,147.
Sep. 30, 2011 Office Action issued in U.S. Appl. No. 12/864,147.
Mar. 12, 2012 Office Action issued in U.S. Appl. No. 12/864,147.
Nov. 14, 2012 Office Action issued in U.S. Appl. No. 13/386,539.
Nov. 14, 2012 Office Action issued in U.S. Appl. No. 13/386,582.
Jan. 31, 2013 Office Action issued in U.S. Appl. No. 13/258,788.
Feb. 22, 2013 Office Action issued in U.S. Appl. No. 13/386,539.
Feb. 22, 2013 Office Action issued in U.S. Appl. No. 13/386,582.
Alexander et al., "The Role of Suppressors of Cytokine Signaling (SOCS) Proteins in Regulation of the Immune Response," Annu. Rev. Immunol., vol. 22, pp. 503-529, 2004.
Larsen et al., "Suppressors of Cytokine Signalling: SOCS," APMIS, vol. 110, pp. 833-844, 2002.
Jun. 18, 2013 Supplementary European Search Report issued in European Application No. 10 82 6811.
Dieterlen-Lievre, "On the Origin of Haemopoietic Stem Cells in the Avian Embryo: An Experimental Approach," J. Embryol. exp. Morph., vol. 33, No. 3, pp. 607-619, 1975.
Aug. 7, 2013 Office Action issued in U.S. Appl. No. 13/258,788.
Aug. 6, 2013 Office Action issued in U.S. Appl. No. 13/386,582.
Selkoe, "Normal and Abnormal Biology of the Beta-Amyloid Precursor Protein," Annu. Rev. Neurosci., vol. 17, pp. 489-517, 1994.
Hayashi et al., "Alzheimer Amyloid Protein Precursor Enhances Proliferation of Neural Stem Cells from Fetal Rat Brain," Biochemical and Biophysical Research Communications, vol. 205, No. 1, pp. 936-943, 1994.
Venkataramani et al., "Histone Deacetylase Inhibitor Valproic Acid Inhibits Cancer Cell Proliferation via Down-Regulation of the Alzheimer Amyloid Precursor Protein," The Journal of Biological Chemistry, vol. 285, No. 14, pp. 10678-10689, Apr. 2, 2010.
Kwak, "Studies on the Novel Function of Amyloid Precursor Protein in Glial Differentiation of Neural Stem Cells," Dissertation, pp. 1-173, 2006.
Oct. 16, 2013 Office Action issued in U.S. Appl. No. 13/701,747.

* cited by examiner

US 8,673,846 B2

CELL PROLIFERATION-PROMOTING PEPTIDE AND USE THEREOF

TECHNICAL FIELD

The present invention relates to a peptide capable of promoting proliferation of stem and other cells; and use thereof. Especially, it relates to a cell proliferation promoter (a composition) containing the peptide and a method to produce cells of interest at an increased proliferation rate using the peptide.

The present application claims priority from Japanese Patent Application No. 2009-252010, filed on Nov. 2, 2009, the entire contents of which are hereby incorporated by reference.

BACKGROUND ART

In the field of regenerative medicine, it has been a challenge to establish a method to proliferate cells of interest at a higher rate. In the fields of cell engineering and fermentation engineering, in order to increase the yield of the cells of interest themselves or to increase the efficiency of the cells (or tissue) of interest to produce products, it is desired to proliferate more efficiently the subject cultured cells (or cells constituting cultured tissue).

Conventionally, for the above purposes, various cell growth factors have been used. One example among the most frequently used growth factors is basic fibroblast growth factor (hereinafter, it may be referred to as "bFGF"). bFGF is known as a substance to exhibit an effect of promoting proliferation of various mesodermal and neuroectodermal cells in addition to fibroblasts and is a growth factor that is frequently used in promoting proliferation of various kinds of subject cells.

However, as the currently available bFGF is very expensive, it is financially difficult to use the growth factor in a relatively large quantity for cell proliferation. Moreover, using bFGF for the purpose of cell proliferation may become a significant cause to increase the cost of cell manufacturing and tissue regeneration involving the said proliferation.

Under these circumstances, research and development of a low-cost, mass-producible substance that has cell proliferation-promoting capability to replace the expensive cell growth factors such as bFGF are underway so far. For example, Patent Documents 1 to 3 listed below respectively describe a peptide that possesses cell proliferation-promoting capability and the respective Patent Literatures describe that by using the peptide, the proliferation rate of the test cells was increased.

CITATION LIST

Patent Literatures

Patent Document 1: Japanese Patent Application Publication No. 2003-137899
Patent Document 2: Japanese Patent Application Publication No. 2005-154338
Patent Document 3: Japanese Patent Application Publication No. 2009-209064
Patent Document 4: Japanese Patent Application Publication No. 2005-330206
Patent Document 5: WO2008/008569

Non-Patent Literatures

Non-Patent Document 1: *EMBO Reports*, Vol. 10, No. 3, pp. 231-238 (2009)
Non-Patent Document 2: *PNAS*, Vol. 95, pp. 114-119 (1998)
Non-Patent Document 3: *Genes & Development*, Vol. 12, pp. 3872-3881 (1998)
Non-Patent Document 4: *Genes & Development*, Vol. 18, pp. 2867-2872 (2004)
Non-Patent Document 5: *Genes & Development*, Vol. 18, pp. 3055-3065 (2004)
Non-Patent Document 6: *Molecular Cell*, Vol. 25, pp. 207-217 (2007)
Non-Patent Document 7: *The Journal of Biological Chemistry*, Vol. 282, No. 51, pp. 37064-37073 (2007)
Non-Patent Document 8: *Cell Cycle*, Vol. 6, No. 6, pp. 656-659 (2007)

SUMMARY OF INVENTION

An objective of the present invention is to provide a peptide having a composition that is different from those of the conventional cell-proliferation-promoting peptides described in Patent Documents 1 to 3, the peptide being an artificial peptide that can exhibit a cell proliferation-promoting effect equal to or greater than bFGF. Another objective is to provide a cell proliferation promoter (pharmaceutical composition) containing such a peptide as an active ingredient. Another objective is to provide a method for producing selected cells of interest using such a peptide.

The cell proliferation promoter provided by this invention is characterized by that it comprises, as an active ingredient (i.e. a substance involved in promoting cell proliferation), at least one kind of the peptide disclosed herein that possesses cell proliferation-promoting capability (hereinafter, it may be referred to as "peptide with cell proliferation-promoting capability").

In other words, the peptide according to this invention that can be used as an active ingredient of the cell proliferation promoter is an artificially synthesized peptide comprising, in its peptide chain, partial amino acid sequences as specified in the following (A) and (B), respectively:
(A) an amino acid sequence constituting a membrane-permeable peptide
(B) an amino acid sequence selected from SEQ ID NOs: 19 to 103 or an amino acid sequence formed by substituting, deleting and/or adding (inserting) one or several (typically, two or three) amino acid residues in the selected amino acid sequence.

Typically, the cell proliferation promoter disclosed herein contains at least one pharmaceutically acceptable carrier (for instance, a base material to contribute to increase the stability of the above peptide or a fluid medium such as saline or a buffer solution).

The present inventors have come to accomplish this invention by finding out that a synthetic peptide constituted by combining a plurality of amino acid sequences, each constituting a peptide that originally exhibits a different activity or a moiety within a selected peptide (i.e. a peptide motif or domain) that had been identified by a specific activity, has an activity to promote cell proliferation that is equal to or greater than that of bFGF.

In other words, the amino acid sequence specified in (A) above is an amino acid sequence of a membrane-permeable peptide; and the amino acid sequence specified in (B) above is, for instance, an amino acid sequence corresponding to a peptide motif that is active as a neural differentiation inducer or a partial C-terminal amino acid sequence of prelamin A which is known as a protein to support nuclear architecture. As illustrative examples of such amino acid sequences, SEQ ID NOs: 19 to 103 are disclosed herein.

Thus, because the cell proliferation promoter disclosed herein comprises, as an active ingredient, a peptide that can be readily produced by an artificial method such as chemical synthesis (or biosynthesis), it can be used (typically as a substitute for bFGF) to promote proliferation of eukaryotic cells of interest without using an expensive cell growth factor such as bFGF or the like in a large quantity. Since it is possible to reduce the use of an expensive cell growth factor like bFGF or others, a cost reduction can be achieved in cell culturing or biologically active substance production that involves cell proliferation; or the cost increase can be suppressed.

In a preferred embodiment, the cell proliferation promoter disclosed herein, as the synthetic peptide (cell proliferation-promoting peptide), comprises a peptide having, as the (A) an amino acid sequence constituting a membrane-permeable peptide, an amino acid sequence selected from SEQ ID NOs: 1 to 18 or an amino acid sequence formed by substituting, deleting and/or adding (inserting) one or several (typically, two or three) amino acid residues in the selected amino acid sequence.

The amino acid sequences represented by SEQ ID NOs: 1 to 18 disclosed herein are typical examples of the above (A) amino acid sequence constituting a membrane-permeable peptide and can be preferably employed in embodiments of the present invention. It is especially preferable to employ one of the amino acid sequences (typically, SEC ID NOs: 1 to 15; especially, SEQ ID NOs: 14 and 15) that are signal sequences to localize a protein in the nucleolus within a nucleus and are known as nucleolar localization signals (NoLSs, see Non-Patent Literature 1).

In another preferred embodiment of the cell proliferation promoter disclosed herein, the synthetic peptide (cell proliferation-promoting peptide) is composed of at most 50 total amino acid residues. Since such a short chain of peptide can be readily prepared by chemical synthesis, and is low-cost and easily handled, it is preferred as an ingredient of a cell proliferation promoter.

In another preferred embodiment of the cell proliferation promoter disclosed herein, the synthetic peptide (cell proliferation-promoting peptide) comprises an amino acid sequence specified in the above (B) attached to the N-terminus or the C-terminus of the amino acid sequence specified in the above (A).

A peptide having such a composition shows especially great cell proliferation-promoting capability. A peptide composed of at most 30 total amino acid residues is especially preferred since its structure is simple and it can be easily obtained by chemical synthesis.

Illustrative examples of the preferred synthetic peptide (cell proliferation-promoting peptide) provided by the present invention include a peptide comprising an amino acid sequence selected from SEQ ID NOs: 104 to 111 (especially, those having at most 50 or at most 30 total amino acid residues), or a peptide consisting of an amino acid sequence selected from SEQ ID NOs: 104 to 111. A cell proliferation promoter comprising such a synthetic peptide (cell proliferation-promoting peptide) is preferable for the purpose of promoting proliferation of cells of human or a non-human mammalian origin (for instance, stem cells of one species).

The present invention, as another aspect, provides a method for manufacturing at least one kind of eukaryotic cells or a biosynthetic substance derived from the eukaryotic cells by proliferating the cells typically in vitro (or in vivo), with the method being characterized by supplying a cell proliferation promoter disclosed herein (in other words, a cell proliferation-promoting peptide disclosed herein) at least once to the eukaryotic cell subjected to proliferation.

According to such a production method, it is possible to reduce the use of an expensive cell growth factor such as bFGF or others; and therefore, a cost reduction can be achieved in cell culturing or biologically active substance production that involves cell proliferation; or the cost increase can be suppressed.

The production method disclosed herein can be preferably carried out in order to facilitate repairing or regeneration of an affected area of a subject (patient). That is, because the method disclosed herein enables efficient in-vitro proliferation of the cells that contribute to repairing or regeneration, the cells efficiently proliferated in vitro by carrying out the present method can be placed internally to the body of a subject (patient), thereby bringing about a reduction in the time for repair or regeneration.

In a preferred embodiment of the production method disclosed herein, the eukaryotic cells are of a human origin or a non-human mammalian origin. The cell proliferation-promoting peptide disclosed herein can be preferably used for promoting proliferation of this type of cells. In particular, preferred examples of the eukaryotic cells include any kind of stem cells in an undifferentiated state.

DESCRIPTION OF EMBODIMENT

Figure 1:
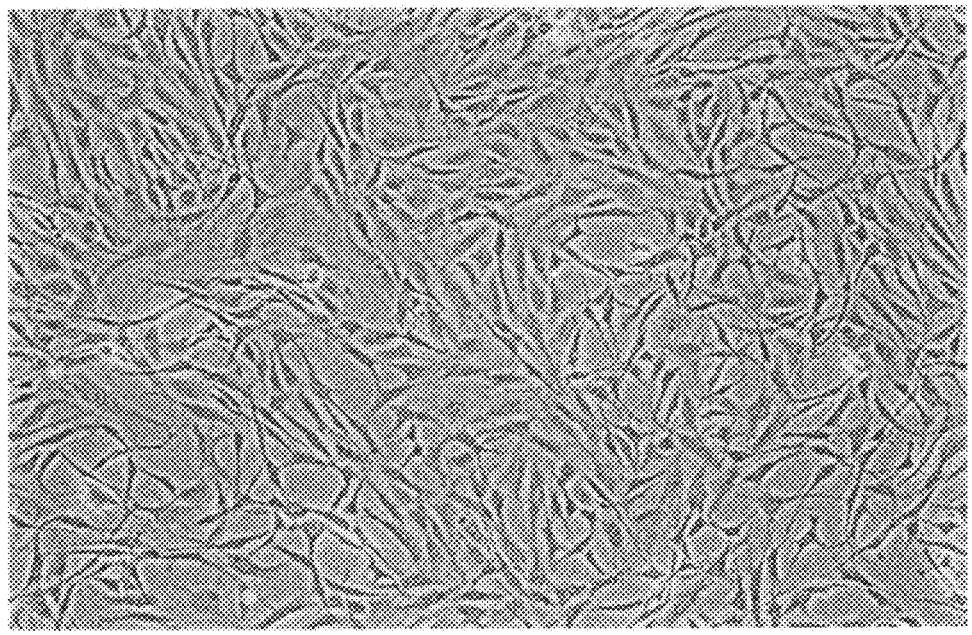
FIG. 1 shows a micrograph image showing the state of cell proliferation when three days had passed from the start of the incubation of undifferentiated rat bone marrow stem cells (mesenchymal stem cells) to which a cell proliferation-promoting peptide of an Example (Sample 1) had been added.

Preferred embodiments of the present invention are described below. Note that technical matters other than those matters particularly mentioned in the present specification (e.g., the primary structure and chain length of a cell proliferation-promoting peptide) which are required for carrying out the present invention (e.g., general matters relating to peptide synthesis, cell cultivation, and preparation of a pharmaceutical composition containing a peptide) are matters of design variation that could be apprehended by a person skilled in the art based on prior art in such fields as cell engineering, medicine, pharmacology, organic chemistry, biochemistry, genetic engineering, protein engineering, molecular biology and hygieiology. The present invention can be practiced based on the technical details disclosed in the present specification and on common general technical knowledge in the pertinent fields. In the following description, amino acids are indicated by single-letter designations (in sequence listings, by three-letter designations) in accordance with the nomenclature for amino acids set forth in the IUPAC-IUB guidelines.

In the amino acid sequences included in the present specification, the left side is always the N-terminus and the right side is the C-terminus.

The present specification incorporates by reference the entire contents of all of the documents cited herein.

In the present specification, "artificially synthesized cell proliferation-promoting peptide" refers to a peptide chain which does not stably exist by itself in nature, and is instead a peptide fragment that is manufactured by artificial chemical synthesis or biosynthesis (i.e., genetic engineering-based production) and can stably exist in a certain system (e.g., in a composition making up a neural cell proliferation promoter).

In this specification, "peptide" is a term which denotes an amino acid polymer having a plurality of peptide bonds, and is not limited by the number of amino acid residues included in the peptide chain, with the term typically referring to one having a relatively small molecular weight with no more than 100, preferably no more than 50 (more preferably no more than 30) amino acid residues in total.

In this specification, unless specified otherwise, "amino acid residue" is a term which includes the N-terminal amino acid and the C-terminal amino acid of a peptide chain. In this specification, "modified amino acid sequence" in relative to a selected amino acid sequence refers to an amino acid sequence formed by substituting, deleting and/or adding (inserting) one or several (typically two or three) amino acid residues without impairing the cell proliferation-promoting capability of the selected amino acid sequence. Typical examples of the modified amino acid sequence referred in the present specification include a sequence generated by conservative amino acid replacement where one or several (typically two or three) amino acid residues are conservatively substituted (e.g., a basic amino acid residue is substituted with a different basic amino acid residue), a sequence corresponding to a selected amino acid sequence with deletion of one or several (typically two or three) amino acid residues, and the like.

In this specification, "polynucleotide" is a term denoting a polymer (nucleic acid) in which a plurality of nucleotides are linked by phosphodiester bonds, and is not limited by the number of nucleotides. As used herein, the term 'polynucleotide' encompasses DNA fragments and RNA fragments of various lengths. "Artificially designed polynucleotide" refers to a polynucleotide whose chain (whole length) does not exist by itself in nature and that is manufactured artificially by chemical synthesis or biosynthesis (i.e., genetic engineering-based production).

The cell proliferation promoter disclosed herein is a composition characterized by that it comprises, as an active ingredient, a synthetic peptide (i.e., a cell proliferation-promoting peptide) discovered by the present inventors to have good cell proliferation-promoting activity against at least one kind of cells (a cell line).

As described above, the cell proliferation-promoting peptide disclosed herein comprises, as a partial amino acid sequence, an amino acid sequence constituting a membrane-permeable peptide as specified in the above (A) (hereinafter, it may be referred to as the "(A) part sequence").

As for the (A) part amino acid sequence, any amino acid sequence constituting a membrane-permeable peptide that can permeate cell membrane and/or nuclear membrane can be used without particular limitation. For instance, the amino acid sequences represented by SEQ ID NOs: 1 to 18 in the sequence table of this specification as well as modified amino acid sequences thereof (limited to those with membrane permeability) are preferred as the amino acid sequence constituting the (A) part sequence. Below are the details.

The amino acid sequence of SEQ ID NO: 1 corresponds to a NoLS composed of 14 total amino acid residues derived from FGF2 (a basic fibroblast growth factor).

The amino acid sequence of SEQ ID NO: 2 corresponds to a NoLS composed of 19 total amino acid residues derived from a type of nucleolar protein (ApLLP).

The amino acid sequence of SEQ ID NO: 3 corresponds to a NoLS composed of 16 total amino acid residues derived from a HSV-1 (herpes simplex virus type 1) protein ($\gamma(1)$ 34.5).

The amino acid sequence of SEQ ID NO: 4 corresponds to a NoLS composed of 19 total amino acid residues derived from HIC p40 protein (human I-mfa domain-containing protein).

The amino acid sequence of SEQ ID NO: 5 corresponds to a NoLS composed of 16 total amino acid residues derived from MEQ, a MDV (Mareles disease virus) protein.

The amino acid sequence of SEQ ID NO: 6 corresponds to a NoLS composed of 17 total amino acid residues derived from survivin Delta-Ex3, an apoptosis suppressor protein.

The amino acid sequence of SEQ ID NO: 7 corresponds to a NoLS composed of 7 total amino acid residues derived from Angiogenin, a vascular growth factor.

The amino acid sequence of SEQ ID NO: 8 corresponds to a NoLS composed of 8 total amino acid residues derived from MDM2, a nuclear phosphoprotein, which forms a complex with a tumor suppressor protein p53.

The amino acid sequence of SEQ ID NO: 9 corresponds to a NoLS composed of 9 total amino acid residues derived from GGNNVα, a betanodavirus protein.

The amino acid sequence of SEQ ID NO: 10 corresponds to a NoLS composed of 7 total amino acid residues derived from NF-κB inducing kinase (NIK).

The amino acid sequence of SEQ ID NO: 11 corresponds to a NoLS composed of 15 total amino acid residues derived from a nuclear VCP-like protein.

The amino acid sequence of SEQ ID NO: 12 corresponds to a NoLS composed of 18 total amino acid residues derived from p120, a nucleolar protein.

The amino acid sequence of SEQ ID NO: 13 corresponds to a NoLS composed of 14 total amino acid residues derived from HVS (herpesvirus saimiri) ORF57 protein.

The amino acid sequence of SEQ ID NO: 14 corresponds to a NoLS composed of 13 total amino acid residues matching with amino acid residue number 491 through 503 of LIM kinase 2, a type of protein kinase present in human endothelial cells and involved in intracellular signaling.

The amino acid sequence of SEQ ID NO: 15 corresponds to a nucleolar localization sequence composed of 8 total amino acid residues contained in N protein (nucleocapsid protein) of IBV (avian infectious bronchitis virus).

The amino acid sequence of SEQ ID NO: 16 corresponds to a membrane-permeable motif composed of 11 total amino acid residues derived from a protein transduction domain of HIV (human immunodeficiency virus) TAT.

The amino acid sequence of SEQ ID NO: 17 corresponds to a membrane-permeable motif composed of 11 total amino acid residues of a protein transduction domain (PTD4) obtained by modification of the TAT.

The amino acid sequence of SEQ ID NO: 18 corresponds to a membrane-permeable motif composed of 18 total amino acid residues derived from ANT of antennapedia which is a drosophila mutant.

Of these, especially preferred are the amino sequences related to NoLS (or modified amino acid sequences thereof). Particularly, NoLS-related amino acid sequences such as those represented by SEQ ID NOs: 14 and 15 are preferable as the (A) part sequence of the cell proliferation-promoting peptide.

On the other hand, the amino acid sequence constituting the (B) part sequence of the cell proliferation-promoting peptide is a sequence (peptide motif) discovered by the present inventors to be able to form a peptide with an excellent cell proliferation-promoting activity when combined with the (A) part sequence and these are listed as SEQ ID NOs 19 to 103. Below are the details.

The amino acid sequences represented by SEQ ID NOs 19 to 36 are amino acid sequences contained in the BC-boxes of various proteins identified as SOCS proteins (See Non-patent Literatures 2 to 5). SOCS protein herein is a collective term of various SOCS (suppressor of cytokine signaling) proteins having a SOCS-box which is a domain that can bind Elongin BC complex (specifically, a part of Elongin C) known to function as a transcription factor by forming a complex with Elongin A, and also family proteins thereof.

Illustrative examples include the amino acid sequences composed of 15 consecutive amino acid residues from the N-terminus of the respective BC-boxes contained in mSOCS-1 (SEQ ID NO: 19), mSOCS-2 (SEQ ID NO: 20), mSOCS-3 (SEQ ID NO: 21), mSOCS-4 (SEQ ID NO: 22), mSOCS-5 (SEQ ID NO: 23), hSOCS-6 (SEQ ID NO: 24), hSOCS-7 (SEQ ID NO: 25), hRAR-1 (SEQ ID NO: 26), hRAR-like (SEQ ID NO: 27), mWSB-1 (SEQ ID NO: 28), mWSB-2 (SEQ ID NO: 29), mASB-1 (SEQ ID NO: 30), mASB-2 (SEQ ID NO: 31), hASB-3 (SEQ ID NO: 32), LRR-1 (SEQ ID NO: 33), hASB-7 (SEQ ID NO: 34), mASB-10 (SEQ ID NO: 35), hASB-14 (SEQ ID NO:36).

Although a detailed description is omitted here, SEQ ID NOs: 37 to 97 correspond to the amino acid sequences contained in the BC-boxes of various SOCS proteins identified from viruses (HIV, AdV, SIV, etc.) and mammals. For example, SEC ID NO: 92 and SEQ ID NO: 96 represent amino acid sequences contained in the BC-box of a SOCS protein identified from human (MUFI). SEQ ID NO: 97 represents an amino acid sequence contained in the BC-box of a SOCS protein, mCIS (cytokine-inducible SH2-containing protein), identified from the mouse.

SEQ ID NO: 98 corresponds to the amino acid sequence composed of 15 total amino acid residues matching with the amino acid residues at the 157th through 171st positions from the N-terminus of the amino acid sequence of a von Hippel-Lindau (VHL) protein known to be expressed specifically in neural cells of the central nervous system (see Patent Document 4).

SEQ ID NOs: 99 to 102 correspond to the amino acid sequences of the WD6 domain of RACK1, which is a HIF-1α-binding protein that binds the PAS-A domain (i.e., the subdomain of Per-Arnt-Sim homology domain) which is one of the two subunits (i.e., HIF-1α and HIF-1β) forming hypoxia inducible factor 1 (HIF-1), and which is also identified as a receptor of activated protein kinase C, thereby corresponding to the amino acid sequences of Elongin C-binding domains (see Non-patent Literature 6 to 8).

SEQ ID NO:103 represents the amino acid sequence composed of 15 total amino acid residues matching with amino acid residues at the 647th through 661st positions from the N-terminus of prelamin A protein, which has been suggested lately to function as a differentiation-inducing signal for stem cells (see Patent Document 5).

The peptide chain (amino acid sequence) of the cell proliferation-promoting peptide disclosed herein is constituted by adequately combining the aforementioned (A) part sequence and (B) part sequence. Either of the (A) part sequence and the (B) part sequence can be located at the C-terminal side (N-terminal side) with respect to each other. It is preferable that the (A) part sequence and the (B) part sequence are located next to each other. In other words, it is preferable that between the (A) part sequence and the (B) part sequence, an amino acid residue that is not included in these sequences is absent, or that only about one to three are present if any.

As for the cell proliferation-promoting peptide, one with at least one amidated amino acid residue is preferable. Amidation of a carboxyl group of an amino acid residue (typically the C-terminal amino acid residue of the peptide chain) may increase the structural stability (e.g., protease resistance).

For as long as the cell proliferation-promoting activity is not lost, a sequence other than the (A) part sequence and the (B) part sequence may be included. Though no particular limitation is imposed on this partial sequence, preferred is one that allows to maintain the 3-dimensional conformation (typically the straight chain conformation) of the (A) part sequence and the (B) part sequence. The total number of amino acid residues in the cell proliferation-promoting peptide is desirable to be not more than 100 and preferable to be not more than 50. Especially preferable is not more than 30. Such a short chain of peptide can be easily prepared by chemical synthesis and the cell proliferation-promoting peptide can be readily provided. Although no particular limitation is imposed on the conformation of the peptide for as long as the cell proliferation-promoting capability is exhibited under a subjected environment (in vitro or in vivo), a linear or helical conformation is preferred from the standpoint that does not readily become an immunogen (antigen). Peptides of these conformations are not likely to form epitopes. From these standpoints, as the cell proliferation-promoting peptide applied to the cell proliferation promoter, a linear peptide with a relatively low molecular weight (typically with at most 50 (especially at most 30) amino acid residues) is preferred.

The proportion of the (A) part sequence and the (B) part sequence in relative to the entire amino acid sequence (i.e., of the total number of amino acid residues constituting the peptide chain, the number % of the amino acid residues constituting the (A) part sequence and the (B) part sequence) is, though not particularly limited for as long as the cell proliferation-promoting activity is not lost, desirably about at least 60% and preferably at least 80%. It is especially preferable to be at least 90%.

It is noted that as for the cell proliferation-promoting peptide of the present invention, a peptide with all amino acid residues being L-amino acids is preferred while for as long as the cell proliferation-promoting activity is not lost, a peptide substituted partially or entirely with D-amino acids may be used.

Of the cell proliferation-promoting peptide disclosed herein, one with a relatively short peptide chain can be easily manufactured according to the conventional chemical synthesis methodologies. For instance, either of the conventional solid-phase synthesis or liquid-phase synthesis can be employed. Solid-phase synthesis where the BOC (t-butoxycarbonyl) or the Fmoc (9-fluorenylmethoxycarbonyl) group is used as the amine protecting group is preferable.

For the cell proliferation-promoting peptide disclosed herein, a peptide chain having a desired amino acid sequence and a portion with modification (e.g., C-terminal amidation) can be synthesized by solid-phase synthesis using a commercial peptide synthesizer (which is, for instance, available from PerSeptive Biosystems, Applied Biosystems, etc.).

Alternatively, the cell proliferation-promoting peptide may be biosynthesized based on a genetic engineering technique. This approach is preferred in cases where a peptide such as a so-called polypeptide that has a relatively long peptide chain is produced. In particular, a DNA having a nucleotide sequence (including the ATG initiation codon) encoding the amino acid sequence of the desired cell proliferation-promoting peptide is synthesized. Then, a recombinant vector having an expression gene construct composed of this DNA and various regulatory elements (including promoters, ribosome binding sites, terminators, enhancers, and various cis-elements which control the expression level) for expressing this amino acid sequence within a host cell is constructed in accordance with the host cell.

Using an ordinary technique, this recombinant vector is inserted into given host cells (e.g., yeasts, insect cells), and the host cells, or tissue or masses containing these cells are cultured under specific conditions. In this way, the target polypeptide can be expressed and produced intracellularly. Then, by isolating from the host cells (when the polypeptide is secreted, from the culture medium) and purifying the polypeptide, the target cell proliferation-promoting peptide can be obtained.

Methods hitherto used in the art may be directly employed without modification as the method for constructing the recombinant vector and the method for introducing the constructed recombinant vector into the host cell. Because such methods themselves are not distinctive to the present invention, detailed descriptions are omitted here.

For example, a fusion protein expression system may be employed for efficient large-scale production in given host cells. That is, a gene (DNA) coding for the amino acid sequence of the subject cell proliferation-promoting peptide is chemically synthesized, and the synthesized gene is introduced to a preferred site on a suitable fusion protein expression vector (e.g., a GST (glutathione S-transferase) fusion protein expression vector such as the pET series available from Novagen and the pGEX series available from Amersham Bioscience). Host cells (typically, *Escherichia coli*) are then transformed by the vector. The resulting transformant is cultured, thereby producing the target fusion protein. This protein is then extracted and purified. Next, the resulting purified fusion protein is cleaved with a specific enzyme (protease), and the liberated target peptide fragments (the designed artificial cell proliferation-promoting peptide) are recovered by a method such as affinity chromatography. The cell proliferation-promoting peptide of the present invention may be produced by using such conventional a fusion protein expression system (e.g., the GST/His system available from Amersham Bioscience may be used).

Alternatively, the target polypeptide may be synthesized in vitro by constructing a template DNA for a cell-free protein synthesis system (i.e., a synthesized gene fragment having a nucleotide sequence which codes for the amino acid sequence of the cell proliferation-promoting peptide) and, using the various compounds required for peptide synthesis (e.g., ATP, RNA polymerase, amino acids, etc.), and employing a cell-free protein synthesis system. For information concerning cell-free protein synthesis systems, reference may be made to, for example, Shimizu et al., *Nature Biotechnology*, 19, 751-755 (2001), and Madin et al., *Proc. Natl. Acad. Sci. USA*, 97 (2), 559-564 (2000). Based on the technology described in these articles, many corporations have been conducting contract manufacturing of polypeptides at the time when this application was filed. Also, wheat germ cell-free protein synthesis kits (such as PROTEIOS™ available from Toyobo Co., Ltd. of Japan) are commercially available.

Therefore, so long as the (A) part sequence and the (B) part sequence have been selected and the peptide chain has been designed, the target cell proliferation-promoting peptide can be easily synthesized and produced by a cell-free protein synthesis system in accordance with the amino acid sequence. For instance, a cell proliferation-promoting peptide of the present invention can be easily produced based on PURESYSTEM® from Post Genome Institute Co., Ltd, of Japan.

A single-stranded or a double-stranded nucleotide sequence encoding the cell proliferation-promoting peptide of the present invention and/or a polynucleotide complementary to the said nucleotide sequence can be produced (synthesized) by a conventionally known method. In other words, a nucleotide sequence corresponding to the amino acid sequence of the cell proliferation-promoting peptide can be easily determined and provided by selecting a codon corresponding to each amino acid residues constituting the designed amino acid sequence. Then, once the nucleotide sequence is determined, a polynucleotide (single strand) corresponding to the desired nucleotide sequence can be easily obtained by utilizing a DNA synthesizer or the like. Furthermore, a target double-stranded DNA can be obtained by using the obtained single strand as a template and employing various enzymatic synthetic methods (typically PCR).

The polynucleotide provided by the present invention may be in the form of DNA or RNA (mRNA or the like). The DNA can be provided in the form of a double strand or a single strand. When it is provided in the form of a single strand, it may be a coding strand (sense strand) or may be an anticoding strand (anti-sense strand) that is complementary thereto.

The polynucleotide provided by the present invention can be used as a material for constructing a recombinant DNA (expression cassette) for expressing a cell proliferation-promoting peptide in various host cells or cell-free protein synthesis systems.

The present invention thus provides a polynucleotide containing a nucleotide sequence encoding a cell proliferation-promoting peptide having a novel amino acid sequence and/or a nucleotide sequence complimentary to the said sequence. For instance, provided is an artificially designed polynucleotide comprising a nucleotide sequence encoding an amino acid sequence that has at most 50 (preferably at most 30) total amino acid residues constituting the peptide chain and is represented by one of SEQ ID NOs: 104 to 111 or an amino acid sequence modified from one of these sequences, or, alternatively provided is an artificially designed polynucleotide comprising a nucleotide sequence encoding an amino acid sequence containing one of the above amino acid sequences and/or a nucleotide sequence complimentary to the said nucleotide sequence, or essentially composed of these nucleotide sequences.

A preferred cell proliferation-promoting peptide of the present invention exhibits cell proliferation-promoting activity toward at least one type of eukaryotic cells (a eukaryotic cell line). Hence, it can be used as an active ingredient of a cell proliferation promoter. The cell proliferation-promoting peptide contained in the cell proliferation promoter can be present as a salt for as long as the cell proliferation-promoting activity is not inhibited. For example, an acid salt of the peptide, which can be obtained by adding a conventionally-used inorganic or organic acid in accordance with an ordinary technique, can be used. Alternatively, while the cell proliferation-promoting activity is maintained, a different type of salt (e.g., a metal salt) can be used. The "peptide" described in this Specification and Claims encompasses those in the salt forms.

The cell proliferation promoter disclosed herein may contain various pharmaceutically (medically) acceptable carriers in accordance with the application form for as long as the cell proliferation-promoting peptide which is the active ingredient is maintained active in promoting cell proliferation. Carriers generally used as diluents or excipients in peptide medications are preferred. Although it may suitably vary depending on the intended purpose and form of the cell proliferation promoter, typical examples include water, physiological buffers and various organic solvents. The carrier may be an aqueous alcohol (ethanol or the like) solution at an appropriate concentration, glycerol, or non-drying oil such as olive oil. Or it may be a liposome. Examples of secondary ingredients that may be contained in the cell proliferation promoter include various fillers, thickeners, binders, wetting agents, surfactants, dyes, fragrances and the like.

The form of the cell proliferation promoter is not subject to any particular limitation. Examples of typical forms include liquid formulas, suspensions, emulsions, aerosols, foams, granules, powders, tablets, capsules, ointments, aqueous gels and the like. For use in injection or the like, the cell proliferation promoter may be rendered into a freeze-dried form or pellets to be prepared into a drug solution by dissolving in saline or a suitable buffer (e.g., PBS) just prior to use.

The process itself of preparing a drug (composition) in various forms by using as the materials the cell proliferation-promoting peptide (main ingredient) and various carriers (secondary ingredients) may be carried out in accordance with a conventional method. Because such a preparation process itself is not distinctive to the present invention, a detailed description is omitted here. An example of a detailed information source relating to formulation is *Comprehensive Medicinal Chemistry*, edited by Corwin Hansch and published by Pergamon Press (1990), the entire contents of which are incorporated in this specification by reference.

The subject cells to which the cell proliferation promoter (cell proliferation-promoting peptide) disclosed herein is applied are not particularly limited, with the promoter being able to enhance the proliferation ability of eukaryotic cells of various living species In particular, cells of a human or a non-human animal (especially a mammal) origin are preferred as the subject. Based on the medical values, stem cells are especially preferred as the subject. Examples of this type of stem cells include embryotic stem cells, induced pluripotent stem cells (iPS cells), mesenchymal stem cells, neural stem cells, myeloid stem cells, hematopoietic stem cells, and the like. Other examples preferred as the subject include somatic cells (dermal fibroblasts, neural cells, vascular endothelial cells and the like) and germ cells. From the standpoint of cell proliferation, using stem cells in an undifferentiated state (stem cells that had not been subjected to differentiation-inducing treatment) is particularly preferable.

The cell proliferation promoter disclosed herein can be used by a method and in a dose according to its form and intended purpose.

For examples, when cells (e.g., an established cell line) are cultured to proliferate in vitro, an appropriate amount of the cell proliferation-promoting peptide (i.e., a cell proliferation promoter containing the said peptide) may be added to the eukaryotic cells subjected to incubation (proliferation) in a culture medium at any time during the incubation process, preferably at the same time as the start of the incubation or at an early time after the incubation start.

The added amount and the number of added portions are not particularly limited as they may vary in accordance with the conditions such as the type of the cultured cells, cell density (initial cell density at the incubation start), passage number, incubation conditions, type of the cultured medium and the like. When commonly-used eukaryotic cells (particularly cells of a mammal including human) are cultured, the peptide is preferably added in one or several portions (for instance, added portion-wise at the start of the incubation and at the same time as a cell passage or culture medium exchange) so that the concentration of the cell proliferation-promoting peptide in the cultured medium be within a range of about 0.1 μM to 100 μM and more preferably within a range of 0.5 μM to 20 μM (e.g., 1 μM to 10 μM).

By adding the cell proliferation-promoter (cell proliferation-promoting peptide) disclosed herein to an in-vitro culturing medium, the subject cells themselves or the biosynthetic substances (e.g., various physiologically-active agents and enzymes) produced by the said cells can be efficiently manufactured. Moreover, since an expensive growth factor such as bFGF or the like is not used or a smaller amount thereof may be used, the manufacturing cost can be reduced.

In another case where cells (e.g., a tissue fragment or a cellular mass transplanted in a specific area) are proliferated in vivo, an appropriate amount of the cell proliferation promoter (i.e., cell proliferation-promoting peptide) disclosed herein can be prepared into a liquid formula and administered by a desired amount to a patient (i.e. in vivo) by intravenous, intramuscular, subcutaneous, intradermal, or intraperitoneal injection. Alternatively, the promoter in a solid form such as tablets, a gel form such as ointment and the like, or an aqueous gel form can be administered directly to an affected area (e.g., body surface such as a burn or a wound). Alternatively, it can be administered orally or in a suppository form. In these ways, the proliferation rate of the subject cells to be grown in vivo, typically in an affected area or its periphery can be increased. The added amount and the number of added portions are not particularly limited as they may vary depending on the conditions such as the type of the cells to be proliferated, present area, and the like.

By administering the cell proliferation promoter (cell proliferation-promoting peptide) disclosed herein to a needy area in vivo, its cell proliferation-promoting activity can enhance nerve regeneration, angiogenesis, skin regeneration or the like. By the increased cell proliferation capability, for instance, anti-aging of skin, early fixation of a transplanted organ, early reparation of a wound or a burn caused by a physical interference such as an traffic accident or the like can be accomplished. Additionally, for example, the promoter can be used as a pharmaceutical composition that contributes to regenerative medicine treatment of neural diseases such as Parkinson's disease, stroke, Alzheimer's disease, body paralysis caused by spinal cord injury, cerebral contusion, amyotrophic lateral sclerosis, Huntington's disease, brain tumor, retinal degeneration and the like.

Alternatively, by adding an appropriate amount of a cell proliferation promoter (cell proliferation-promoting peptide) to a cellular material removed temporarily or permanently from an organism, i.e., a living tissue or a cellular mass (e.g., a material cultured from somatic stem cells), the subject cells (even some tissue or an organ) can be efficiently produced in vitro without using a large amount of an expensive growth factor such as bFGF or the like.

By placing the subject cells (or some tissue or an organ in which the number of cells had been increased) that had been efficiently produced (proliferated) in vitro by employing the cell production method (in-vitro cell production method) or the cell proliferation promoter disclosed herein to a lesion (i.e., inside a patient's body) where repair or regeneration is needed, the time required for the repair or the regeneration can be reduced.

Several examples of the present invention are described below, although these examples are not intended to limit the scope of the invention.

Example 1

Peptide Synthesis

A total of eleven different peptides (Samples 1 to 11) were prepared using the subsequently described peptide synthesizer. Table 1 lists the details of the amino acid sequences of these synthesized peptides.

TABLE 1

| Sample No. | Amino acid sequence | Total number of amino acid residues |
|---|---|---|
| 1 | TLKERCLQVVRSLVK KKRTLRKNDRKKR (SEQ ID NO: 104) | 28 |
| 2 | TLDGGDIINALCFS KKRTLRKNDRKKR (SEQ ID NO: 105) | 27 |
| 3 | KKRTLRKNDRKKR LLGNSSPRTQSPQNC (SEQ ID NO: 106) | 28 |
| 4 | KKRTLRKNDRKKR TLKERCLQVVRSLVK (SEQ ID NO: 107) | 28 |
| 5 | YARAAARQARA TLKERCLQVVRSLVK (SEQ ID NO: 108) | 26 |
| 6 | WRRQARFK TLKERCLQVVRSLVK (SEQ ID NO: 109) | 23 |
| 7 | YGRKKRRQRRRTLKERCLQVVRSLVK (SEQ ID NO: 110) | 26 |
| 8 | YARAAARQARA SLQYLCRFVIRQYTR (SEQ ID NO: 111) | 26 |
| 9 | KKRTLRKNDRKKR (SEQ ID NO: 14) | 13 |
| 10 | YARAAARQARA (SEQ ID NO: 17) | 11 |
| 11 | WRRQARFK (SEQ ID NO: 15) | 8 |

As shown in Table 1, Sample 1 (SEQ ID NO: 104) is a peptide composed of 28 total amino acid residues, having as the (B) part sequence at the N-terminus the amino acid sequence derived from a VHL protein, which is denoted as SEQ ID NO: 98, and as the (A) part sequence attached thereto on the C-terminal side the amino acid sequence (NoLS) derived from LIM kinase 2, which is denoted as SEQ ID NO: 14.

Sample 2 (SEQ ID NO: 105) is a peptide composed of 27 total amino acid residues, having as the (B) part sequence at the N-terminus the amino acid sequence derived from RACK 1, which is denoted as SEQ ID NO: 99, and as the (A) part sequence attached thereto on the C-terminal side the amino acid sequence (NoLS) derived from LIM kinase 2, which is denoted as SEQ ID NO: 14.

Sample 3 (SEQ ID NO: 106) is a peptide composed of 28 total amino acid residues, having as the (A) part sequence at the N-terminus the amino acid sequence (NoLS) derived from LIM kinase 2, which is denoted as SEQ ID NO: 14, and as the (B) part sequence attached thereto on the C-terminal side the amino acid sequence derived from prelamin A, which is denoted as SEQ ID NO: 103.

Sample 4 (SEQ ID NO: 107) is a peptide composed of 28 total amino acid residues, having as the (A) part sequence at the N-terminus the amino acid sequence (NoLS) derived from LIM kinase 2, which is denoted as SEQ ID NO: 14, and as the (B) part sequence attached thereto on the C-terminal side the amino acid sequence derived from a VHL protein, which is denoted as SEQ ID NO: 98.

Sample 5 (SEQ ID NO: 108) is a peptide composed of 26 total amino acid residues, having as the (A) part sequence at the N-terminus the amino acid sequence derived from PTD4, which is denoted as SEQ ID NO: 17, and as the (B) part sequence attached thereto on the C-terminal side the amino acid sequence derived from a VHL protein, which is denoted as SEQ ID NO: 98.

Sample 6 (SEQ ID NO: 109) is a peptide composed of 23 total amino acid residues, having as the (A) part sequence at the N-terminus the amino acid sequence derived from N-protein of IBV, which is denoted as SEQ ID NO: 15, and as the (B) part sequence attached thereto on the C-terminal side the amino acid sequence derived from a VHL protein, which is denoted as SEQ ID NO: 98.

Sample 7 (SEQ ID NO: 110) is a peptide composed of 26 total amino acid residues, having as (A) part sequence at the N-terminus the amino acid sequence derived from HIV TAT, which is denoted as SEQ ID NO: 16, and as the (B) part sequence attached thereto on the C-terminal side the amino acid sequence derived from a VHL protein, which is denoted as SEQ ID NO: 98.

Sample 8 (SEQ ID NO: 111) is a peptide composed of 26 total amino acid residues, having as the (A) part sequence at the N-terminus the amino acid sequence derived from PTD4, which is denoted as SEQ ID NO: 17, and as the (B) part sequence attached thereto on the C-terminal side the amino acid sequence derived from hSOCS, which is denoted as SEQ ID NO: 24.

As shown in Table 1, Sample 9 is a peptide composed of 13 total amino acid residues, having only the amino acid sequence derived from LIM kinase 2 denoted as SEQ ID NO: 14, which is an (A) part sequence.

Sample 10 is a peptide composed of 11 total amino acid residues, having only the amino acid sequence of PTD4 denoted as SEQ ID NO: 17, which is an (A) part sequence.

Sample 11 is a peptide composed of 11 total amino acid residues, having only the amino acid sequence derived from N-protein of IBV denoted as SEQ ID NO: 15, which is an (A) part sequence.

In all of these peptides, the carboxyl group (—COOH) of the C-terminal amino acid is amidated (—CONH$_2$). Each of these peptides was synthesized by solid-phase synthesis (Fmoc chemistry) using a commercial peptide synthesizer (an intavis AG system) in accordance with its operation manual. Because the mode of using a peptide synthesizer itself is not distinctive to the present invention, a detailed description is omitted here.

Example 2

Evaluation of Synthesized Peptides On Cell Proliferation-Promoting Activity

The cell proliferation-promoting peptides (Samples 1 to 8) obtained in Example 1 and the peptides composed of only a (A) part sequence (Samples 9 to 11) which had been prepared for comparison were evaluated, respectively, on the cell proliferation-promoting activity. Sample 12 was an experimental control where a commercial bFGF was used as the cell proliferation promoter. Sample 13 was an experimental control where no peptide was added (bFGF was not added, either). The evaluation assay is described in detail below. Each synthesized peptide sample was dissolved in PBS (phosphate buffered saline) to prepare a stock solution having a peptide concentration of 1 mM.

Rat bone marrow stem cells (mesenchymal stem cells) were used as the test cells. In particular, the test stem cells were subcultured in Dulbecco MEM (DMEM: a Gibco product) containing 10% fetal bovine serum (FBS: a Gibco product), 2 mM of L-glutamine, 50 unit/mL of penicillin, and 50 µg/mL of streptomycin. Passage 2 cells were used for the evaluation.

The test stem cells that had been pre-incubated overnight in the DMEM containing 10 ng/mL of bFGF were collected and seeded at $1 \times 10^3$ cells per well in a 96-well plate. The amount of the culture medium was 100 mL per well.

Then, the stock solutions containing respective peptides of Samples 1 to 11 were added to some wells, one for each well. For comparison, a commercial bFGF (a PeproTech product) was added at a concentration of 10 ng/mL to some other wells (Sample 12). Similarly, yet some other wells were set up to not to contain any of the sample peptides or bFGF (Sample 13).

After a sample peptide or bFGF was added as described above, the 96-well plate was placed in a $CO_2$ incubator and incubated standing at 37° C. and 5% $CO_2$. Exchange of the culture medium was carried out every other day. The culture medium used for an exchange was the same as the culture medium used initially for the incubation (i.e., for the group containing a sample peptide or bFGF, the same sample peptide or bFGF was added to the exchanged culture medium).

During the course of this incubation assay, water-soluble tetrazolium salt (WST-8) was added to some wells as a staining reagent at the start of the incubation (day 0), when two days had passed from the start (day 2) and when four days had passed from the start (day 4). Incubated for 2 hours after the addition, the cell culture medium with the added staining reagent was collected. The level of cell proliferation was evaluated by colorimetry as optical density measured at 450 nm ($OD_{450}$) based on reduction of the tetrazolium salt. The results are shown in Table 2.

TABLE 2

| Sample No. | $OD_{450}$ Start | day 2 | day 4 |
|---|---|---|---|
| 1 | 0.124 | 1.264 | 2.369 |
| 2 | 0.124 | 1.133 | 2.259 |
| 3 | 0.124 | 1.177 | 2.289 |
| 4 | 0.124 | 1.357 | 2.410 |
| 5 | 0.124 | 0.926 | 1.971 |
| 6 | 0.124 | 1.181 | 2.365 |
| 7 | 0.124 | 1.340 | 2.279 |
| 8 | 0.124 | 0.856 | 1.828 |
| 9 | 0.124 | 0.648 | 1.260 |
| 10 | 0.124 | 0.770 | 1.737 |
| 11 | 0.124 | 0.799 | 1.744 |
| 12 | 0.124 | 1.022 | 1.977 |
| 13 | 0.124 | 0.534 | 1.379 |

Figure 2:
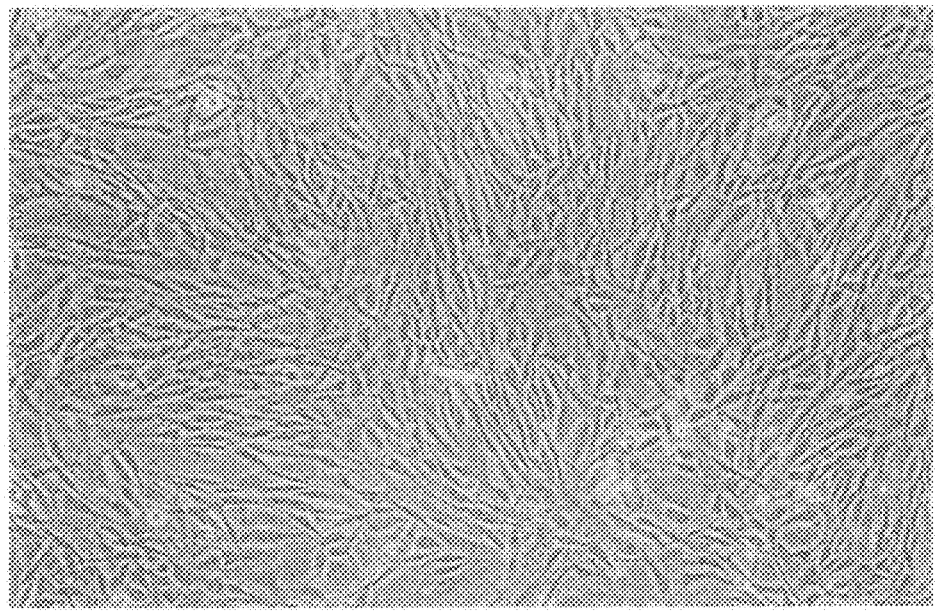
FIG. 2 shows a micrograph image showing the state of cell proliferation when three days had passed from the start of the incubation of undifferentiated rat bone marrow stem cells (mesenchymal stem cells) to which a cell proliferation-promoting peptide of an Example (Sample 2) had been added.
Figure 3:
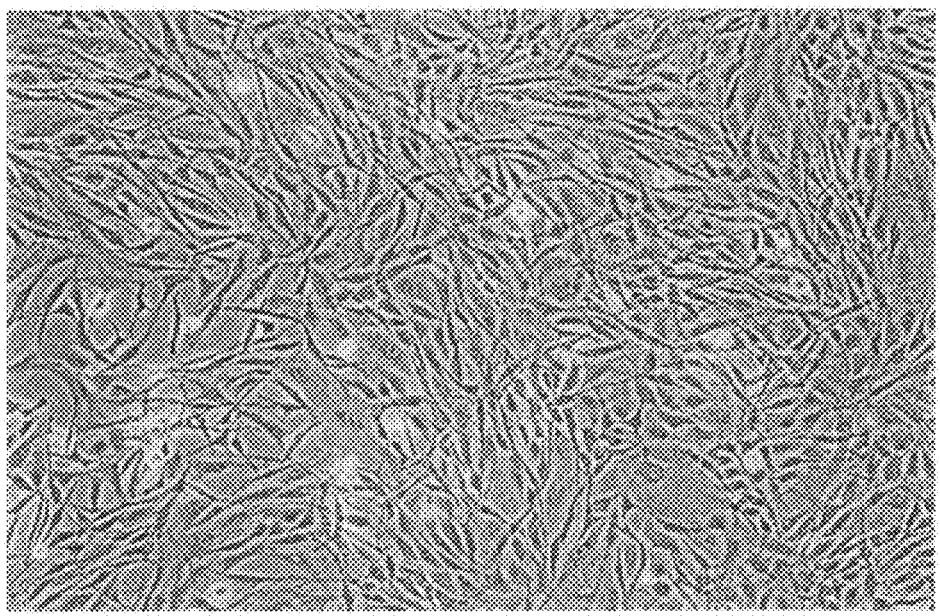
FIG. 3 shows a micrograph image showing the state of cell proliferation when three days had passed from the start of the incubation of undifferentiated rat bone marrow stem cells (mesenchymal stem cells) to which a cell proliferation-promoting peptide of an Example (Sample 3) had been added.
Figure 4:
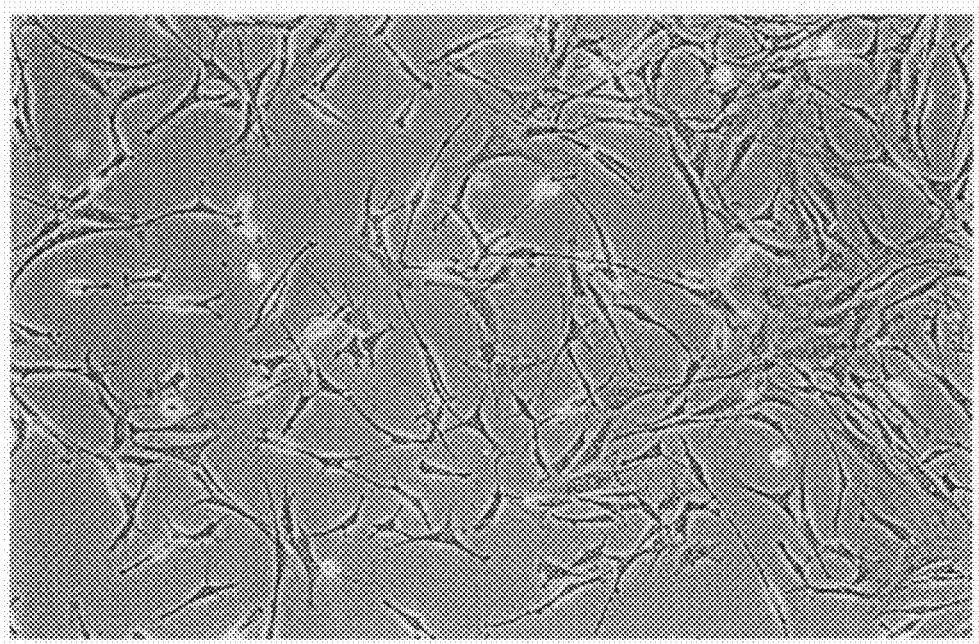
FIG. 4 shows, as a comparative example, a micrograph image showing the state of cell proliferation when three days had passed from the start of the incubation of undifferentiated rat bone marrow stem cells (mesenchymal stem cells) to which neither a cell proliferation-promoting peptide nor bFGF had been added.

As apparent from the optical densities shown in Table 2, the cultures to which the respective cell proliferation-promoting peptides (Samples 1 to 8) disclosed herein were added showed cell proliferation-promoting ability equal to or greater than that of the culture with added bFGF (Sample 12). This indicates that these sample peptides have notably great cell proliferation-promoting activities. Especially, the peptides containing, as the (A) part sequence, a NoLS-derived amino acid sequence (e.g., Samples 1 to 4 and 6) or a TAT-derived amino acid sequence as the (A) part sequence (Sample 7) exhibited particularly significant cell proliferation-promoting activities. FIG. 1, FIG. 2 and FIG. 3, respectively, show micrograph images taken when three days had passed from the start of incubation. When these micrograph images are compared to the micrograph of FIG. 4 which was taken about the culture of Sample 13 (i.e. the culture containing no peptide) when three days had passed from the start of incubation, the high cell proliferation-promoting activity of the cell proliferation-promoting peptide disclosed herein was visually confirmed.

Although detailed data are not shown here, when the test stem cells proliferated and produced in these examples were collected and, with a use of commercial materials, subjected to a bone differentiation-inducing treatment generally conducted on this type of stem cells, normal bone differentiation was observed. This indicates that the cell proliferation-promoting peptide (cell proliferation promoter) disclosed herein can enhance normal cell proliferation without causing any abnormal alteration (e.g., cancerous change) to the cells subjected to proliferation.

Example 3

Preparation of Granular Formulation 50 mg of Sample 1 peptide was mixed with 50 mg of crystalized cellulose and 400 mg of lactose. 1 mL of an ethanol-water solution was added thereto and the resultant was mixed well. The resulting mixture was prepared into granules according to a conventional method and a granular formulation containing as the primary ingredient, a cell proliferation-promoting peptide (i.e., a cell proliferation promoter in granules) was obtained.

INDUSTRIAL APPLICABILITY

As described above, the cell proliferation-promoting peptide disclosed herein exhibits a high cell proliferation-promoting activity; and therefore, it is useful as a substitute for an expensive cell growth factor such as bFGF or the like. A cell proliferation promoter containing this peptide can be utilized, for example, as a composition for medicinal purposes.

SEQUENCE LISTING FREE TEXT

SEQ ID NO: 1 to SEQ ID No: 111 Synthetic peptides

What is claimed is:

1. A composition for promoting proliferation of at least one kind of eukaryotic cells, the composition comprising:
    an artificially synthesized peptide with cell proliferation-promoting capability;
    and
    a pharmaceutically acceptable carrier;
    wherein
    the synthesized peptide comprises:
    (A) the amino acid sequence of SEQ ID NO:14 directly attached to the C-terminus of (B) the amino acid sequence of SEQ ID NO:99.

2. The composition according to claim 1, wherein the synthesized peptide is composed of at most 50 total amino acid residues.

3. The composition according to claim 1, wherein the synthesized peptide is composed of at most 30 total amino acid residues.

4. The composition according to claim 1, wherein the synthesized peptide comprises the amino acid sequence of SEQ ID NO:105.

5. The composition according to claim 1, wherein the synthesized peptide consists of the amino acid sequence of SEQ ID NO:105.

6. A method for manufacturing at least one kind of eukaryotic cells or a biosynthetic substance from the eukaryotic cells by proliferating the cells, the method comprising:
    incubating the eukaryotic cells in a culture medium; and
    adding the composition of claim 1 to the culture medium during the incubation process.

7. The method according to claim 6, wherein the synthesized peptide is composed of at most 50 total amino acid residues.

8. The method according to claim 6, wherein the synthesized peptide is composed of at most 30 total amino acid residues.

9. The method according to claim 6, wherein the synthesized peptide comprises the amino acid sequence of SEQ ID NO:105.

10. The method according to claim 6, wherein the synthesized peptide consists of the amino acid sequence of SEQ ID NO:105.

11. The method according to claim 6, wherein the eukaryotic cells are of a human origin or a non-human mammalian origin.

12. The method according to claim 11, wherein the eukaryotic cells are stem cells in an undifferentiated state.

* * * * *

```
                              SEQUENCE LISTING

<160> NUMBER OF SEQ ID NOS: 111

<210> SEQ ID NO 1
<211> LENGTH: 14
<212> TYPE: PRT
<213> ORGANISM: Artificial sequence
<220> FEATURE:
<223> OTHER INFORMATION: Synthetic Construct

<400> SEQUENCE: 1

Arg Ser Arg Lys Tyr Thr Ser Trp Tyr Val Ala Leu Lys Arg
1               5                   10

<210> SEQ ID NO 2
<211> LENGTH: 19
<212> TYPE: PRT
<213> ORGANISM: Artificial sequence
<220> FEATURE:
<223> OTHER INFORMATION: Synthetic Construct

<400> SEQUENCE: 2

Met Ala Lys Ser Ile Arg Ser Lys His Arg Arg Gln Met Arg Met Met
1               5                   10                  15

Lys Arg Glu

<210> SEQ ID NO 3
<211> LENGTH: 16
<212> TYPE: PRT
<213> ORGANISM: Artificial sequence
<220> FEATURE:
<223> OTHER INFORMATION: Synthetic Construct

<400> SEQUENCE: 3

Met Ala Arg Arg Arg Arg His Arg Gly Pro Arg Arg Pro Arg Pro Pro
1               5                   10                  15

<210> SEQ ID NO 4
<211> LENGTH: 19
<212> TYPE: PRT
<213> ORGANISM: Artificial sequence
<220> FEATURE:
<223> OTHER INFORMATION: Synthetic Construct

<400> SEQUENCE: 4

Gly Arg Cys Arg Arg Leu Ala Asn Phe Gly Pro Arg Lys Arg Arg Arg
1               5                   10                  15

Arg Arg Arg

<210> SEQ ID NO 5
<211> LENGTH: 16
<212> TYPE: PRT
<213> ORGANISM: Artificial sequence
<220> FEATURE:
<223> OTHER INFORMATION: Synthetic Construct

<400> SEQUENCE: 5

Arg Arg Arg Lys Arg Asn Arg Asp Ala Arg Arg Arg Arg Arg Lys Gln
1               5                   10                  15

<210> SEQ ID NO 6
```

```
<211> LENGTH: 17
<212> TYPE: PRT
<213> ORGANISM: Artificial sequence
<220> FEATURE:
<223> OTHER INFORMATION: Synthetic Construct

<400> SEQUENCE: 6

Met Gln Arg Lys Pro Thr Ile Arg Arg Lys Asn Leu Arg Leu Arg Arg
1               5                   10                  15
Lys

<210> SEQ ID NO 7
<211> LENGTH: 7
<212> TYPE: PRT
<213> ORGANISM: Artificial sequence
<220> FEATURE:
<223> OTHER INFORMATION: Synthetic Construct

<400> SEQUENCE: 7

Ile Met Arg Arg Arg Gly Leu
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic Construct

<400> SEQUENCE: 8

Lys Lys Leu Lys Lys Arg Asn Lys
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic Construct

<400> SEQUENCE: 9

Arg Arg Arg Ala Asn Asn Arg Arg Arg
1               5

<210> SEQ ID NO 10
<211> LENGTH: 7
<212> TYPE: PRT
<213> ORGANISM: Artificial sequence
<220> FEATURE:
<223> OTHER INFORMATION: Synthetic Construct

<400> SEQUENCE: 10

Arg Lys Lys Arg Lys Lys Lys
1               5

<210> SEQ ID NO 11
<211> LENGTH: 15
<212> TYPE: PRT
<213> ORGANISM: Artificial sequence
<220> FEATURE:
<223> OTHER INFORMATION: Synthetic Construct

<400> SEQUENCE: 11

Lys Arg Lys Gly Lys Leu Lys Asn Lys Gly Ser Lys Arg Lys Lys
1               5                   10                  15

<210> SEQ ID NO 12
```

```
<211> LENGTH: 18
<212> TYPE: PRT
<213> ORGANISM: Artificial sequence
<220> FEATURE:
<223> OTHER INFORMATION: Synthetic Construct

<400> SEQUENCE: 12

Ser Lys Arg Leu Ser Ser Arg Ala Arg Lys Arg Ala Ala Lys Arg Arg
1               5                   10                  15

Leu Gly

<210> SEQ ID NO 13
<211> LENGTH: 14
<212> TYPE: PRT
<213> ORGANISM: Artificial sequence
<220> FEATURE:
<223> OTHER INFORMATION: Synthetic Construct

<400> SEQUENCE: 13

Lys Arg Pro Arg Arg Arg Pro Ser Arg Pro Phe Arg Lys Pro
1               5                   10

<210> SEQ ID NO 14
<211> LENGTH: 13
<212> TYPE: PRT
<213> ORGANISM: Artificial sequence
<220> FEATURE:
<223> OTHER INFORMATION: Synthetic Construct

<400> SEQUENCE: 14

Lys Lys Arg Thr Leu Arg Lys Asn Asp Arg Lys Lys Arg
1               5                   10

<210> SEQ ID NO 15
<211> LENGTH: 8
<212> TYPE: PRT
<213> ORGANISM: Artificial sequence
<220> FEATURE:
<223> OTHER INFORMATION: Synthetic Construct

<400> SEQUENCE: 15

Trp Arg Arg Gln Ala Arg Phe Lys
1               5

<210> SEQ ID NO 16
<211> LENGTH: 11
<212> TYPE: PRT
<213> ORGANISM: Artificial sequence
<220> FEATURE:
<223> OTHER INFORMATION: Synthetic Construct

<400> SEQUENCE: 16

Tyr Gly Arg Lys Lys Arg Arg Gln Arg Arg Arg
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic Construct

<400> SEQUENCE: 17

Tyr Ala Arg Ala Ala Ala Arg Gln Ala Arg Ala
1               5                   10

<210> SEQ ID NO 18
```

```
<211> LENGTH: 18
<212> TYPE: PRT
<213> ORGANISM: Artificial sequence
<220> FEATURE:
<223> OTHER INFORMATION: Synthetic Construct

<400> SEQUENCE: 18

Lys Gly Arg Gln Val Lys Val Trp Phe Gln Asn Arg Arg Met Lys Trp
1               5                   10                  15

Lys Lys

<210> SEQ ID NO 19
<211> LENGTH: 15
<212> TYPE: PRT
<213> ORGANISM: Artificial sequence
<220> FEATURE:
<223> OTHER INFORMATION: Synthetic Construct

<400> SEQUENCE: 19

Pro Leu Gln Glu Leu Cys Arg Gln Arg Ile Val Ala Ala Val Gly
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: Synthetic Construct

<400> SEQUENCE: 20

Thr Leu Gln His Phe Cys Arg Leu Ala Ile Asn Lys Cys Thr Gly
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: Synthetic Construct

<400> SEQUENCE: 21

Thr Leu Gln His Leu Cys Arg Lys Thr Val Asn Gly His Leu Asp
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: Synthetic Construct

<400> SEQUENCE: 22

Ser Leu Gln His Ile Cys Arg Thr Val Ile Cys Asn Cys Thr Thr
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: Synthetic Construct

<400> SEQUENCE: 23

Ser Leu Gln Tyr Ile Cys Arg Ala Val Ile Cys Arg Cys Thr Thr
1               5                   10                  15

<210> SEQ ID NO 24
```

```
<211> LENGTH: 15
<212> TYPE: PRT
<213> ORGANISM: Artificial sequence
<220> FEATURE:
<223> OTHER INFORMATION: Synthetic Construct

<400> SEQUENCE: 24

Ser Leu Gln Tyr Leu Cys Arg Phe Val Ile Arg Gln Tyr Thr Arg
1               5                   10                  15

<210> SEQ ID NO 25
<211> LENGTH: 15
<212> TYPE: PRT
<213> ORGANISM: Artificial sequence
<220> FEATURE:
<223> OTHER INFORMATION: Synthetic Construct

<400> SEQUENCE: 25

Ser Leu Gln His Leu Cys Arg Phe Arg Ile Arg Gln Leu Val Arg
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Synthetic Construct

<400> SEQUENCE: 26

Ser Leu Gln Asp Leu Cys Cys Arg Ala Val Val Ser Cys Thr Pro
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: Synthetic Construct

<400> SEQUENCE: 27

Ser Leu Gln Asp Leu Cys Cys Arg Thr Ile Val Ser Cys Thr Pro
1               5                   10                  15

<210> SEQ ID NO 28
<211> LENGTH: 15
<212> TYPE: PRT
<213> ORGANISM: Artificial sequence
<220> FEATURE:
<223> OTHER INFORMATION: Synthetic Construct

<400> SEQUENCE: 28

Ser Leu Gln His Ile Cys Arg Met Ser Ile Arg Arg Val Met Ser
1               5                   10                  15

<210> SEQ ID NO 29
<211> LENGTH: 15
<212> TYPE: PRT
<213> ORGANISM: Artificial sequence
<220> FEATURE:
<223> OTHER INFORMATION: Synthetic Construct

<400> SEQUENCE: 29

Ser Leu Lys His Leu Cys Arg Lys Ala Leu Arg Ser Phe Leu Thr
1               5                   10                  15

<210> SEQ ID NO 30
<211> LENGTH: 15
<212> TYPE: PRT
```

<213> ORGANISM: Artificial sequence
<220> FEATURE:
<223> OTHER INFORMATION: Synthetic Construct

<400> SEQUENCE: 30

Thr Leu Leu Ser Leu Cys Arg Val Ala Val Arg Arg Ala Leu Gly
1               5                   10                  15

<210> SEQ ID NO 31
<211> LENGTH: 15
<212> TYPE: PRT
<213> ORGANISM: Artificial sequence
<220> FEATURE:
<223> OTHER INFORMATION: Synthetic Construct

<400> SEQUENCE: 31

Pro Leu Ala His Leu Cys Arg Leu Arg Val Arg Lys Ala Ile Gly
1               5                   10                  15

<210> SEQ ID NO 32
<211> LENGTH: 15
<212> TYPE: PRT
<213> ORGANISM: Artificial sequence
<220> FEATURE:
<223> OTHER INFORMATION: Synthetic Construct

<400> SEQUENCE: 32

Ser Leu Thr His Leu Cys Arg Leu Glu Ile Arg Ser Ser Ile Lys
1               5                   10                  15

<210> SEQ ID NO 33
<211> LENGTH: 15
<212> TYPE: PRT
<213> ORGANISM: Artificial sequence
<220> FEATURE:
<223> OTHER INFORMATION: Synthetic Construct

<400> SEQUENCE: 33

Thr Leu Leu Glu Ser Ser Ala Arg Thr Ile Leu His Asn Arg Ile
1               5                   10                  15

<210> SEQ ID NO 34
<211> LENGTH: 15
<212> TYPE: PRT
<213> ORGANISM: Artificial sequence
<220> FEATURE:
<223> OTHER INFORMATION: Synthetic Construct

<400> SEQUENCE: 34

Asn Leu Gln Asp Leu Cys Arg Ile Lys Ile Arg Gln Cys Ile Gly
1               5                   10                  15

<210> SEQ ID NO 35
<211> LENGTH: 15
<212> TYPE: PRT
<213> ORGANISM: Artificial sequence
<220> FEATURE:
<223> OTHER INFORMATION: Synthetic Construct

<400> SEQUENCE: 35

Ser Leu Gln His Leu Cys Arg Cys Ala Leu Arg Ser His Leu Glu
1               5                   10                  15

<210> SEQ ID NO 36
<211> LENGTH: 15
<212> TYPE: PRT
<213> ORGANISM: Artificial sequence
<220> FEATURE:

<223> OTHER INFORMATION: Synthetic Construct

<400> SEQUENCE: 36

Ser Leu Lys His Leu Cys Arg Leu Lys Ile Arg Lys Cys Met Gly
1               5                   10                  15

<210> SEQ ID NO 37
<211> LENGTH: 15
<212> TYPE: PRT
<213> ORGANISM: Artificial sequence
<220> FEATURE:
<223> OTHER INFORMATION: Synthetic Construct

<400> SEQUENCE: 37

Pro Leu Gln Glu Leu Cys Arg Gln Arg Ile Val Ala Thr Val Gly
1               5                   10                  15

<210> SEQ ID NO 38
<211> LENGTH: 15
<212> TYPE: PRT
<213> ORGANISM: Artificial sequence
<220> FEATURE:
<223> OTHER INFORMATION: Synthetic Construct

<400> SEQUENCE: 38

Pro Leu Ala His Leu Cys Arg Leu Arg Val Arg Lys Ala Ile Gly
1               5                   10                  15

<210> SEQ ID NO 39
<211> LENGTH: 15
<212> TYPE: PRT
<213> ORGANISM: Artificial sequence
<220> FEATURE:
<223> OTHER INFORMATION: Synthetic Construct

<400> SEQUENCE: 39

Ser Leu Gln His Leu Cys Arg Met Ser Ile Arg Arg Val Met Pro
1               5                   10                  15

<210> SEQ ID NO 40
<211> LENGTH: 15
<212> TYPE: PRT
<213> ORGANISM: Artificial sequence
<220> FEATURE:
<223> OTHER INFORMATION: Synthetic Construct

<400> SEQUENCE: 40

Ser Leu Gln Asp Leu Cys Cys Arg Ala Val Val Ser Cys Thr Pro
1               5                   10                  15

<210> SEQ ID NO 41
<211> LENGTH: 15
<212> TYPE: PRT
<213> ORGANISM: Artificial sequence
<220> FEATURE:
<223> OTHER INFORMATION: Synthetic Construct

<400> SEQUENCE: 41

Ser Leu Gln Tyr Leu Ala Leu Thr Ala Leu Ile Thr Pro Lys Lys
1               5                   10                  15

<210> SEQ ID NO 42
<211> LENGTH: 15
<212> TYPE: PRT
<213> ORGANISM: Artificial sequence
<220> FEATURE:
<223> OTHER INFORMATION: Synthetic Construct

```
<400> SEQUENCE: 42

Ser Leu Gln Phe Leu Ala Leu Thr Val Tyr Thr Asp Phe Leu Arg
1               5                   10                  15

<210> SEQ ID NO 43
<211> LENGTH: 15
<212> TYPE: PRT
<213> ORGANISM: Artificial sequence
<220> FEATURE:
<223> OTHER INFORMATION: Synthetic Construct

<400> SEQUENCE: 43

Ser Leu Gln Tyr Leu Ala Leu Arg Val Tyr Thr Asn Gly Leu Arg
1               5                   10                  15

<210> SEQ ID NO 44
<211> LENGTH: 15
<212> TYPE: PRT
<213> ORGANISM: Artificial sequence
<220> FEATURE:
<223> OTHER INFORMATION: Synthetic Construct

<400> SEQUENCE: 44

Ser Leu Gln Leu Leu Ala Leu Val Ala Tyr Thr Asn Gly Ile Arg
1               5                   10                  15

<210> SEQ ID NO 45
<211> LENGTH: 15
<212> TYPE: PRT
<213> ORGANISM: Artificial sequence
<220> FEATURE:
<223> OTHER INFORMATION: Synthetic Construct

<400> SEQUENCE: 45

Ser Leu Gln Tyr Leu Ala Leu Leu Ala His Gln Asn Gly Leu Arg
1               5                   10                  15

<210> SEQ ID NO 46
<211> LENGTH: 15
<212> TYPE: PRT
<213> ORGANISM: Artificial sequence
<220> FEATURE:
<223> OTHER INFORMATION: Synthetic Construct

<400> SEQUENCE: 46

Ser Leu Gln Tyr Leu Ala Leu Gln Val Tyr Leu Lys Asp Gly Gly
1               5                   10                  15

<210> SEQ ID NO 47
<211> LENGTH: 15
<212> TYPE: PRT
<213> ORGANISM: Artificial sequence
<220> FEATURE:
<223> OTHER INFORMATION: Synthetic Construct

<400> SEQUENCE: 47

Ser Leu Gln Tyr Leu Ala Ile Lys Ala Trp Ala Arg Gln Gln Leu
1               5                   10                  15

<210> SEQ ID NO 48
<211> LENGTH: 15
<212> TYPE: PRT
<213> ORGANISM: Artificial sequence
<220> FEATURE:
<223> OTHER INFORMATION: Synthetic Construct

<400> SEQUENCE: 48
```

```
Ser Leu Gln Tyr Leu Ala Leu Lys Val Val Ser Asp Val Arg Ser
1               5                   10                  15
```

<210> SEQ ID NO 49
<211> LENGTH: 15
<212> TYPE: PRT
<213> ORGANISM: Artificial sequence
<220> FEATURE:
<223> OTHER INFORMATION: Synthetic Construct

<400> SEQUENCE: 49

```
Ser Leu Gln Tyr Leu Ala Leu Thr Val Val Ser His Val Arg Ser
1               5                   10                  15
```

<210> SEQ ID NO 50
<211> LENGTH: 15
<212> TYPE: PRT
<213> ORGANISM: Artificial sequence
<220> FEATURE:
<223> OTHER INFORMATION: Synthetic Construct

<400> SEQUENCE: 50

```
Ser Leu Gln Phe Leu Ala Leu Val Val Val Gln Gln Asn Gly Arg
1               5                   10                  15
```

<210> SEQ ID NO 51
<211> LENGTH: 15
<212> TYPE: PRT
<213> ORGANISM: Artificial sequence
<220> FEATURE:
<223> OTHER INFORMATION: Synthetic Construct

<400> SEQUENCE: 51

```
Ser Leu Gln Phe Leu Ala Leu Arg Val Val Gln Glu Gly Lys Asn
1               5                   10                  15
```

<210> SEQ ID NO 52
<211> LENGTH: 15
<212> TYPE: PRT
<213> ORGANISM: Artificial sequence
<220> FEATURE:
<223> OTHER INFORMATION: Synthetic Construct

<400> SEQUENCE: 52

```
Ser Leu Gln Phe Leu Ala Leu Gln Val Val Gln Lys Gly His Gly
1               5                   10                  15
```

<210> SEQ ID NO 53
<211> LENGTH: 15
<212> TYPE: PRT
<213> ORGANISM: Artificial sequence
<220> FEATURE:
<223> OTHER INFORMATION: Synthetic Construct

<400> SEQUENCE: 53

```
Ser Leu Gln Phe Leu Cys Leu Arg Val Leu His Gly Gln Gln Glu
1               5                   10                  15
```

<210> SEQ ID NO 54
<211> LENGTH: 15
<212> TYPE: PRT
<213> ORGANISM: Artificial sequence
<220> FEATURE:
<223> OTHER INFORMATION: Synthetic Construct

<400> SEQUENCE: 54

```
Ser Leu Gln Phe Leu Cys Leu Arg Gln Leu Gln His Val Gln Asn
1               5                   10                  15
```

-continued

<210> SEQ ID NO 55
<211> LENGTH: 15
<212> TYPE: PRT
<213> ORGANISM: Artificial sequence
<220> FEATURE:
<223> OTHER INFORMATION: Synthetic Construct

<400> SEQUENCE: 55

Ser Leu Gln Phe Leu Cys Leu Arg Gln Leu Gln His Val Gln Ser
1               5                   10                  15

<210> SEQ ID NO 56
<211> LENGTH: 15
<212> TYPE: PRT
<213> ORGANISM: Artificial sequence
<220> FEATURE:
<223> OTHER INFORMATION: Synthetic Construct

<400> SEQUENCE: 56

Ser Leu Gln Tyr Leu Cys Leu Arg Gln Leu Gln His Val Gln Thr
1               5                   10                  15

<210> SEQ ID NO 57
<211> LENGTH: 15
<212> TYPE: PRT
<213> ORGANISM: Artificial sequence
<220> FEATURE:
<223> OTHER INFORMATION: Synthetic Construct

<400> SEQUENCE: 57

Ser Leu Gln Phe Ile Cys Leu Arg Gln Leu Gln His Val Gln Ala
1               5                   10                  15

<210> SEQ ID NO 58
<211> LENGTH: 15
<212> TYPE: PRT
<213> ORGANISM: Artificial sequence
<220> FEATURE:
<223> OTHER INFORMATION: Synthetic Construct

<400> SEQUENCE: 58

Ser Leu Gln Phe Leu Cys Leu Arg Val Ile Tyr Gly Pro Glu Glu
1               5                   10                  15

<210> SEQ ID NO 59
<211> LENGTH: 15
<212> TYPE: PRT
<213> ORGANISM: Artificial sequence
<220> FEATURE:
<223> OTHER INFORMATION: Synthetic Construct

<400> SEQUENCE: 59

Thr Leu Gln Phe Leu Cys Leu Gln Ala Tyr Leu Arg Gly Arg Lys
1               5                   10                  15

<210> SEQ ID NO 60
<211> LENGTH: 15
<212> TYPE: PRT
<213> ORGANISM: Artificial sequence
<220> FEATURE:
<223> OTHER INFORMATION: Synthetic Construct

<400> SEQUENCE: 60

Thr Leu Gln Leu Leu Cys Leu Arg Ala Tyr Ile Lys Phe Cys Arg
1               5                   10                  15

```
<210> SEQ ID NO 61
<211> LENGTH: 15
<212> TYPE: PRT
<213> ORGANISM: Artificial sequence
<220> FEATURE:
<223> OTHER INFORMATION: Synthetic Construct

<400> SEQUENCE: 61

Ser Leu Gln Cys Ile Ala Gly Gly Gln Val Leu Ala Ser Trp Phe
1               5                   10                  15

<210> SEQ ID NO 62
<211> LENGTH: 15
<212> TYPE: PRT
<213> ORGANISM: Artificial sequence
<220> FEATURE:
<223> OTHER INFORMATION: Synthetic Construct

<400> SEQUENCE: 62

Ser Leu Gln Cys Met Ser Ala Gly Met Leu Leu Gly Arg Trp Phe
1               5                   10                  15

<210> SEQ ID NO 63
<211> LENGTH: 15
<212> TYPE: PRT
<213> ORGANISM: Artificial sequence
<220> FEATURE:
<223> OTHER INFORMATION: Synthetic Construct

<400> SEQUENCE: 63

Ser Leu Gln Cys Met Ala Gly Gly Ala Val Leu Ala Val Trp Phe
1               5                   10                  15

<210> SEQ ID NO 64
<211> LENGTH: 15
<212> TYPE: PRT
<213> ORGANISM: Artificial sequence
<220> FEATURE:
<223> OTHER INFORMATION: Synthetic Construct

<400> SEQUENCE: 64

Ser Leu Gln Cys Ile Ala Gly Gly Gln Val Leu Ala Ser Trp Phe
1               5                   10                  15

<210> SEQ ID NO 65
<211> LENGTH: 15
<212> TYPE: PRT
<213> ORGANISM: Artificial sequence
<220> FEATURE:
<223> OTHER INFORMATION: Synthetic Construct

<400> SEQUENCE: 65

Ser Leu Gln Cys Arg Ala Gly Gly Thr Leu Leu Ala Val Trp Phe
1               5                   10                  15

<210> SEQ ID NO 66
<211> LENGTH: 15
<212> TYPE: PRT
<213> ORGANISM: Artificial sequence
<220> FEATURE:
<223> OTHER INFORMATION: Synthetic Construct

<400> SEQUENCE: 66

Ser Leu Arg Cys Met Ala Gly Gly Ala Val Leu Ala Leu Trp Phe
1               5                   10                  15

<210> SEQ ID NO 67
<211> LENGTH: 15
```

```
<212> TYPE: PRT
<213> ORGANISM: Artificial sequence
<220> FEATURE:
<223> OTHER INFORMATION: Synthetic Construct

<400> SEQUENCE: 67

Ser Leu Gln Cys Lys Ala Gly Gly Val Val Leu Ala Asn Trp Phe
1               5                   10                  15

<210> SEQ ID NO 68
<211> LENGTH: 15
<212> TYPE: PRT
<213> ORGANISM: Artificial sequence
<220> FEATURE:
<223> OTHER INFORMATION: Synthetic Construct

<400> SEQUENCE: 68

Ser Leu Arg Cys Met Ala Gly Gly Ala Val Leu Ala Leu Trp Phe
1               5                   10                  15

<210> SEQ ID NO 69
<211> LENGTH: 15
<212> TYPE: PRT
<213> ORGANISM: Artificial sequence
<220> FEATURE:
<223> OTHER INFORMATION: Synthetic Construct

<400> SEQUENCE: 69

Ser Leu Arg Cys Met Ala Gly Gly Ala Val Leu Ala Leu Trp Phe
1               5                   10                  15

<210> SEQ ID NO 70
<211> LENGTH: 15
<212> TYPE: PRT
<213> ORGANISM: Artificial sequence
<220> FEATURE:
<223> OTHER INFORMATION: Synthetic Construct

<400> SEQUENCE: 70

Ser Leu Arg Cys Met Ala Gly Gly Ala Val Leu Ala Leu Trp Phe
1               5                   10                  15

<210> SEQ ID NO 71
<211> LENGTH: 15
<212> TYPE: PRT
<213> ORGANISM: Artificial sequence
<220> FEATURE:
<223> OTHER INFORMATION: Synthetic Construct

<400> SEQUENCE: 71

Ser Leu Gln Cys Ile Ala Gly Gly Ala Val Leu Ala Ile Trp Phe
1               5                   10                  15

<210> SEQ ID NO 72
<211> LENGTH: 15
<212> TYPE: PRT
<213> ORGANISM: Artificial sequence
<220> FEATURE:
<223> OTHER INFORMATION: Synthetic Construct

<400> SEQUENCE: 72

Ser Leu Gln Cys Leu Ser Ala Thr Gln Val Leu Lys Glu Phe Leu
1               5                   10                  15

<210> SEQ ID NO 73
<211> LENGTH: 15
<212> TYPE: PRT
<213> ORGANISM: Artificial sequence
```

```
<220> FEATURE:
<223> OTHER INFORMATION: Synthetic Construct

<400> SEQUENCE: 73

Ser Leu Gln Cys Arg Ala Met Arg Arg Ile Leu Leu His Val Ile
1               5                   10                  15

<210> SEQ ID NO 74
<211> LENGTH: 15
<212> TYPE: PRT
<213> ORGANISM: Artificial sequence
<220> FEATURE:
<223> OTHER INFORMATION: Synthetic Construct

<400> SEQUENCE: 74

Ser Leu Gln Cys Leu Ala Ala Lys Gln Val Leu Leu Lys Cys Phe
1               5                   10                  15

<210> SEQ ID NO 75
<211> LENGTH: 15
<212> TYPE: PRT
<213> ORGANISM: Artificial sequence
<220> FEATURE:
<223> OTHER INFORMATION: Synthetic Construct

<400> SEQUENCE: 75

Ser Leu Gln Cys Leu Ala Ala Lys Ser Val Leu Leu Ser Cys Phe
1               5                   10                  15

<210> SEQ ID NO 76
<211> LENGTH: 17
<212> TYPE: PRT
<213> ORGANISM: Artificial sequence
<220> FEATURE:
<223> OTHER INFORMATION: Synthetic Construct

<400> SEQUENCE: 76

Ser Leu Gln Tyr Leu Ala Leu Lys Ala Leu Val Thr Pro Lys Lys Ile
1               5                   10                  15

Lys

<210> SEQ ID NO 77
<211> LENGTH: 17
<212> TYPE: PRT
<213> ORGANISM: Artificial sequence
<220> FEATURE:
<223> OTHER INFORMATION: Synthetic Construct

<400> SEQUENCE: 77

Ser Leu Gln Tyr Leu Ala Leu Ala Ala Leu Ile Thr Pro Lys Lys Ile
1               5                   10                  15

Lys

<210> SEQ ID NO 78
<211> LENGTH: 17
<212> TYPE: PRT
<213> ORGANISM: Artificial sequence
<220> FEATURE:
<223> OTHER INFORMATION: Synthetic Construct

<400> SEQUENCE: 78

Ser Leu Gln Tyr Leu Ala Leu Thr Ala Leu Ile Lys Pro Lys Lys Ile
1               5                   10                  15

Lys
```

```
<210> SEQ ID NO 79
<211> LENGTH: 17
<212> TYPE: PRT
<213> ORGANISM: Artificial sequence
<220> FEATURE:
<223> OTHER INFORMATION: Synthetic Construct

<400> SEQUENCE: 79

Ser Leu Gln Tyr Leu Ala Leu Thr Ala Leu Ile Thr Pro Lys Lys Ile
1               5                   10                  15

Lys

<210> SEQ ID NO 80
<211> LENGTH: 17
<212> TYPE: PRT
<213> ORGANISM: Artificial sequence
<220> FEATURE:
<223> OTHER INFORMATION: Synthetic Construct

<400> SEQUENCE: 80

Ser Leu Gln Tyr Leu Ala Leu Lys Ala Leu Val Thr Pro Thr Arg Thr
1               5                   10                  15

Arg

<210> SEQ ID NO 81
<211> LENGTH: 17
<212> TYPE: PRT
<213> ORGANISM: Artificial sequence
<220> FEATURE:
<223> OTHER INFORMATION: Synthetic Construct

<400> SEQUENCE: 81

Ser Leu Gln Tyr Leu Ala Leu Thr Ala Leu Val Ala Pro Lys Lys Thr
1               5                   10                  15

Lys

<210> SEQ ID NO 82
<211> LENGTH: 17
<212> TYPE: PRT
<213> ORGANISM: Artificial sequence
<220> FEATURE:
<223> OTHER INFORMATION: Synthetic Construct

<400> SEQUENCE: 82

Thr Leu Gln Leu Leu Ala Leu Arg Ala Val Val Lys Ala Arg Ser Arg
1               5                   10                  15

Lys

<210> SEQ ID NO 83
<211> LENGTH: 17
<212> TYPE: PRT
<213> ORGANISM: Artificial sequence
<220> FEATURE:
<223> OTHER INFORMATION: Synthetic Construct

<400> SEQUENCE: 83

Thr Leu Gln Phe Leu Ala Leu Lys Ala Val Val Lys Val Lys Arg Asn
1               5                   10                  15

Lys

<210> SEQ ID NO 84
<211> LENGTH: 17
<212> TYPE: PRT
<213> ORGANISM: Artificial sequence
<220> FEATURE:
```

<223> OTHER INFORMATION: Synthetic Construct

<400> SEQUENCE: 84

Thr Leu Gln Tyr Leu Ala Leu Thr Ala Trp Val Gly Ala Lys Lys Arg
1               5                   10                  15
Lys

<210> SEQ ID NO 85
<211> LENGTH: 17
<212> TYPE: PRT
<213> ORGANISM: Artificial sequence
<220> FEATURE:
<223> OTHER INFORMATION: Synthetic Construct

<400> SEQUENCE: 85

Ser Leu Gln Phe Leu Ala Leu Lys Ala Leu Ile Ser Glu Arg Arg His
1               5                   10                  15
Arg

<210> SEQ ID NO 86
<211> LENGTH: 17
<212> TYPE: PRT
<213> ORGANISM: Artificial sequence
<220> FEATURE:
<223> OTHER INFORMATION: Synthetic Construct

<400> SEQUENCE: 86

Ser Leu Gln Phe Leu Ala Leu Lys Ala Leu Val Gly Gln Ser Lys Arg
1               5                   10                  15
Arg

<210> SEQ ID NO 87
<211> LENGTH: 17
<212> TYPE: PRT
<213> ORGANISM: Artificial sequence
<220> FEATURE:
<223> OTHER INFORMATION: Synthetic Construct

<400> SEQUENCE: 87

Ser Leu Gln Tyr Leu Ala Leu Arg Ala Trp Val Arg Val Gly Lys Lys
1               5                   10                  15
Lys

<210> SEQ ID NO 88
<211> LENGTH: 15
<212> TYPE: PRT
<213> ORGANISM: Artificial sequence
<220> FEATURE:
<223> OTHER INFORMATION: Synthetic Construct

<400> SEQUENCE: 88

Pro Leu Met Asp Leu Cys Arg Arg Ser Val Arg Leu Ala Leu Gly
1               5                   10                  15

<210> SEQ ID NO 89
<211> LENGTH: 15
<212> TYPE: PRT
<213> ORGANISM: Artificial sequence
<220> FEATURE:
<223> OTHER INFORMATION: Synthetic Construct

<400> SEQUENCE: 89

Ser Leu Leu His Leu Ser Arg Leu Cys Val Arg His Asn Leu Gly
1               5                   10                  15

<210> SEQ ID NO 90
<211> LENGTH: 15
<212> TYPE: PRT
<213> ORGANISM: Artificial sequence
<220> FEATURE:
<223> OTHER INFORMATION: Synthetic Construct

<400> SEQUENCE: 90

Pro Leu Met Asp Leu Cys Arg Arg Ser Ile Arg Ser Ala Leu Gly
1               5                   10                  15

<210> SEQ ID NO 91
<211> LENGTH: 15
<212> TYPE: PRT
<213> ORGANISM: Artificial sequence
<220> FEATURE:
<223> OTHER INFORMATION: Synthetic Construct

<400> SEQUENCE: 91

Ser Leu Gln Asp Leu Cys Cys Arg Ala Ile Val Ser Cys Thr Pro
1               5                   10                  15

<210> SEQ ID NO 92
<211> LENGTH: 15
<212> TYPE: PRT
<213> ORGANISM: Artificial sequence
<220> FEATURE:
<223> OTHER INFORMATION: Synthetic Construct

<400> SEQUENCE: 92

Ala Leu Phe Glu Leu Cys Gly Arg Ala Val Ser Ala His Met Gly
1               5                   10                  15

<210> SEQ ID NO 93
<211> LENGTH: 11
<212> TYPE: PRT
<213> ORGANISM: Artificial sequence
<220> FEATURE:
<223> OTHER INFORMATION: Synthetic Construct

<400> SEQUENCE: 93

Ser Leu Gln Cys Ile Ala Gly Gly Gln Val Leu
1               5                   10

<210> SEQ ID NO 94
<211> LENGTH: 11
<212> TYPE: PRT
<213> ORGANISM: Artificial sequence
<220> FEATURE:
<223> OTHER INFORMATION: Synthetic Construct

<400> SEQUENCE: 94

Ser Leu Gln His Leu Cys Arg Leu Val Ile Asn
1               5                   10

<210> SEQ ID NO 95
<211> LENGTH: 11
<212> TYPE: PRT
<213> ORGANISM: Artificial sequence
<220> FEATURE:
<223> OTHER INFORMATION: Synthetic Construct

<400> SEQUENCE: 95

Ser Leu Asn Lys Met Cys Ser Asn Leu Leu Glu
1               5                   10

<210> SEQ ID NO 96

```
<211> LENGTH: 14
<212> TYPE: PRT
<213> ORGANISM: Artificial sequence
<220> FEATURE:
<223> OTHER INFORMATION: Synthetic Construct

<400> SEQUENCE: 96

Leu Phe Glu Leu Cys Gly Arg Ala Val Ser Ala His Met Gly
1               5                   10

<210> SEQ ID NO 97
<211> LENGTH: 15
<212> TYPE: PRT
<213> ORGANISM: Artificial sequence
<220> FEATURE:
<223> OTHER INFORMATION: Synthetic Construct

<400> SEQUENCE: 97

Ser Leu Gln His Leu Cys Arg Leu Val Ile Asn Arg Leu Val Ala
1               5                   10                  15

<210> SEQ ID NO 98
<211> LENGTH: 15
<212> TYPE: PRT
<213> ORGANISM: Artificial sequence
<220> FEATURE:
<223> OTHER INFORMATION: Synthetic Construct

<400> SEQUENCE: 98

Thr Leu Lys Glu Arg Cys Leu Gln Val Val Arg Ser Leu Val Lys
1               5                   10                  15

<210> SEQ ID NO 99
<211> LENGTH: 14
<212> TYPE: PRT
<213> ORGANISM: Artificial sequence
<220> FEATURE:
<223> OTHER INFORMATION: Synthetic Construct

<400> SEQUENCE: 99

Thr Leu Asp Gly Gly Asp Ile Ile Asn Ala Leu Cys Phe Ser
1               5                   10

<210> SEQ ID NO 100
<211> LENGTH: 14
<212> TYPE: PRT
<213> ORGANISM: Artificial sequence
<220> FEATURE:
<223> OTHER INFORMATION: Synthetic Construct

<400> SEQUENCE: 100

Thr Leu Asp Gly Gly Asp Val Ile Asn Ala Leu Cys Phe Ser
1               5                   10

<210> SEQ ID NO 101
<211> LENGTH: 22
<212> TYPE: PRT
<213> ORGANISM: Artificial sequence
<220> FEATURE:
<223> OTHER INFORMATION: Synthetic Construct

<400> SEQUENCE: 101

Leu Tyr Thr Leu Asp Gly Gly Asp Ile Ile Asn Ala Leu Cys Phe Ser
1               5                   10                  15

Pro Asn Arg Tyr Trp Leu
            20
```

```
<210> SEQ ID NO 102
<211> LENGTH: 22
<212> TYPE: PRT
<213> ORGANISM: Artificial sequence
<220> FEATURE:
<223> OTHER INFORMATION: Synthetic Construct

<400> SEQUENCE: 102

Leu Tyr Thr Leu Asp Gly Gly Asp Val Ile Asn Ala Leu Cys Phe Ser
1               5                   10                  15

Pro Asn Arg Tyr Trp Leu
            20

<210> SEQ ID NO 103
<211> LENGTH: 15
<212> TYPE: PRT
<213> ORGANISM: Artificial sequence
<220> FEATURE:
<223> OTHER INFORMATION: Synthetic Construct

<400> SEQUENCE: 103

Leu Leu Gly Asn Ser Ser Pro Arg Thr Gln Ser Pro Gln Asn Cys
1               5                   10                  15

<210> SEQ ID NO 104
<211> LENGTH: 28
<212> TYPE: PRT
<213> ORGANISM: Artificial sequence
<220> FEATURE:
<223> OTHER INFORMATION: Synthetic Construct

<400> SEQUENCE: 104

Thr Leu Lys Glu Arg Cys Leu Gln Val Val Arg Ser Leu Val Lys Lys
1               5                   10                  15

Lys Arg Thr Leu Arg Lys Asn Asp Arg Lys Lys Arg
            20                  25

<210> SEQ ID NO 105
<211> LENGTH: 27
<212> TYPE: PRT
<213> ORGANISM: Artificial sequence
<220> FEATURE:
<223> OTHER INFORMATION: Synthetic Construct

<400> SEQUENCE: 105

Thr Leu Asp Gly Gly Asp Ile Ile Asn Ala Leu Cys Phe Ser Lys Lys
1               5                   10                  15

Arg Thr Leu Arg Lys Asn Asp Arg Lys Lys Arg
            20                  25

<210> SEQ ID NO 106
<211> LENGTH: 28
<212> TYPE: PRT
<213> ORGANISM: Artificial sequence
<220> FEATURE:
<223> OTHER INFORMATION: Synthetic Construct

<400> SEQUENCE: 106

Lys Lys Arg Thr Leu Arg Lys Asn Asp Arg Lys Lys Arg Leu Leu Gly
1               5                   10                  15

Asn Ser Ser Pro Arg Thr Gln Ser Pro Gln Asn Cys
            20                  25

<210> SEQ ID NO 107
<211> LENGTH: 28
<212> TYPE: PRT
```

```
<213> ORGANISM: Artificial sequence
<220> FEATURE:
<223> OTHER INFORMATION: Synthetic Construct

<400> SEQUENCE: 107

Lys Lys Arg Thr Leu Arg Lys Asn Asp Arg Lys Lys Arg Thr Leu Lys
1               5                   10                  15
Glu Arg Cys Leu Gln Val Val Arg Ser Leu Val Lys
            20                  25

<210> SEQ ID NO 108
<211> LENGTH: 26
<212> TYPE: PRT
<213> ORGANISM: Artificial sequence
<220> FEATURE:
<223> OTHER INFORMATION: Synthetic Construct

<400> SEQUENCE: 108

Tyr Ala Arg Ala Ala Ala Arg Gln Ala Arg Ala Thr Leu Lys Glu Arg
1               5                   10                  15
Cys Leu Gln Val Val Arg Ser Leu Val Lys
            20                  25

<210> SEQ ID NO 109
<211> LENGTH: 23
<212> TYPE: PRT
<213> ORGANISM: Artificial sequence
<220> FEATURE:
<223> OTHER INFORMATION: Synthetic Construct

<400> SEQUENCE: 109

Trp Arg Arg Gln Ala Arg Phe Lys Thr Leu Lys Glu Arg Cys Leu Gln
1               5                   10                  15
Val Val Arg Ser Leu Val Lys
            20

<210> SEQ ID NO 110
<211> LENGTH: 26
<212> TYPE: PRT
<213> ORGANISM: Artificial sequence
<220> FEATURE:
<223> OTHER INFORMATION: Synthetic Construct

<400> SEQUENCE: 110

Tyr Gly Arg Lys Lys Arg Arg Gln Arg Arg Arg Thr Leu Lys Glu Arg
1               5                   10                  15
Cys Leu Gln Val Val Arg Ser Leu Val Lys
            20                  25

<210> SEQ ID NO 111
<211> LENGTH: 26
<212> TYPE: PRT
<213> ORGANISM: Artificial sequence
<220> FEATURE:
<223> OTHER INFORMATION: Synthetic Construct

<400> SEQUENCE: 111

Tyr Ala Arg Ala Ala Ala Arg Gln Ala Arg Ala Ser Leu Gln Tyr Leu
1               5                   10                  15
Cys Arg Phe Val Ile Arg Gln Tyr Thr Arg
            20                  25
```